United States Patent
Fischer et al.

(10) Patent No.: US 12,076,068 B2
(45) Date of Patent: Sep. 3, 2024

(54) ABLATION APPLICATOR WITH A MATRIX FILLED WITH PARTICLES

(71) Applicant: AFREEZE GMBH, Innsbruck (AT)

(72) Inventors: Gerald Fischer, Völs (AT); Florian Hintringer, Ampass (AT)

(73) Assignee: Afreeze GmbH, Innsbruck (AT)

( * ) Notice: Subject to any disclaimer, the term of this patent is extended or adjusted under 35 U.S.C. 154(b) by 273 days.

(21) Appl. No.: 17/461,498

(22) Filed: Aug. 30, 2021

(65) Prior Publication Data

US 2021/0386468 A1    Dec. 16, 2021

Related U.S. Application Data

(63) Continuation of application No. 15/908,689, filed on Feb. 28, 2018, now Pat. No. 11,103,296, which is a
(Continued)

(30) Foreign Application Priority Data

Jul. 14, 2011  (EP) .................................... 11174062

(51) Int. Cl.
*A61B 18/02*    (2006.01)
*A61M 13/00*    (2006.01)
(Continued)

(52) U.S. Cl.
CPC .......... *A61B 18/0218* (2013.01); *A61B 18/02* (2013.01); *A61M 13/00* (2013.01);
(Continued)

(58) Field of Classification Search
CPC ................ A61B 18/0218; A61B 18/02; A61B 2018/00089; A61B 2018/00214;
(Continued)

(56) References Cited

U.S. PATENT DOCUMENTS

| 4,314,559 A | 2/1982 | Allen |
| 5,281,213 A | 1/1994 | Milder et al. |

(Continued)

FOREIGN PATENT DOCUMENTS

| EP | 2236253 A | 4/1991 |
| EP | 1356779 A1 | 10/2003 |

(Continued)

OTHER PUBLICATIONS

Lemmon, Eric W. et al., "Short Fundamental Equations of State for 20 Industrial Fluids", Journal of Chemical Engineering Data 51: 785-850 (2006) published on web Nov. 4, 2006, 66 pages.

(Continued)

*Primary Examiner* — Michael F Peffley
*Assistant Examiner* — Bo Ouyang
(74) *Attorney, Agent, or Firm* — Lewis Roca Rothgerber Christie LLP

(57) ABSTRACT

An ablation applicator for an ablation device for ablating tissue of a blood vessel having a tubular body defining an inner lumen to which an ablation medium is conductible, a control mechanism for converting the tubular body between a passive operation mode for inserting the ablation applicator into the blood vessel and an active operation mode for ablating tissue of the blood vessel, and an ablation medium supply line for supplying the ablation medium to the inner lumen and positioned within the inner lumen and having a number of openings for passing the ablation medium from the ablation medium supply line to the inner lumen for thermally contacting the ablation medium with the tubular body wherein at least some of the openings are distributed along the ablation medium supply line with a predetermined spacing between neighboring openings. The ablation device can include a first temperature sensor arranged within the inner lumen and an ablation medium return line inside the (Continued)

tubular body made from a material that defines the active shape of the applicator.

18 Claims, 14 Drawing Sheets

Related U.S. Application Data continuation-in-part of application No. 14/232,886, filed as application No. PCT/EP2012/063847 on Jul. 13, 2012, now Pat. No. 9,918,772.

(51) Int. Cl.
    *A61B 18/00* (2006.01)
    *A61M 25/00* (2006.01)

(52) U.S. Cl.
    CPC ............ *A61B 2018/00089* (2013.01); *A61B 2018/00214* (2013.01); *A61B 2018/00285* (2013.01); *A61B 2018/00351* (2013.01); *A61B 2018/00357* (2013.01); *A61B 2018/00375* (2013.01); *A61B 2018/00511* (2013.01); *A61B 2018/00541* (2013.01); *A61B 2018/00577* (2013.01); *A61B 2018/00791* (2013.01); *A61B 2018/00797* (2013.01); *A61B 2018/00839* (2013.01); *A61B 2018/0212* (2013.01); *A61B 2018/0262* (2013.01); *A61B 2218/007* (2013.01); *A61M 25/007* (2013.01); *A61M 2202/0283* (2013.01); *A61M 2202/064* (2013.01)

(58) Field of Classification Search
    CPC .......... A61B 2018/00285; A61B 2018/00351; A61B 2018/00357; A61B 2018/00375; A61M 13/00; A61M 25/007; A61M 2202/0283; A61M 2202/064
    See application file for complete search history.

(56) References Cited

U.S. PATENT DOCUMENTS

| | | | |
|---|---|---|---|
| 5,423,807 | A | 6/1995 | Milder |
| 5,901,783 | A | 5/1999 | Dobak et al. |
| 6,182,666 | B1 | 2/2001 | Dobak |
| 6,241,722 | B1 | 6/2001 | Dobak |
| 6,589,234 | B2 | 7/2003 | Lalonde et al. |
| 6,602,247 | B2* | 8/2003 | Lalonde ............... A61B 18/02 606/22 |
| 6,629,417 | B2 | 10/2003 | Haas et al. |
| 6,979,331 | B2 | 12/2005 | Hintringer et al. |
| 8,387,402 | B2 | 3/2013 | Littrup et al. |
| 8,740,891 | B2 | 6/2014 | Babkin et al. |
| 8,740,892 | B2 | 6/2014 | Babkin et al. |
| 2002/0052613 | A1 | 5/2002 | Ferrera et al. |
| 2002/0120258 | A1 | 8/2002 | Lalonde |
| 2003/0036749 | A1 | 2/2003 | Durkin et al. |
| 2004/0260271 | A1 | 12/2004 | Huyser et al. |
| 2006/0106298 | A1 | 5/2006 | Ahmed et al. |
| 2006/0247611 | A1 | 11/2006 | Abboud et al. |
| 2007/0016174 | A1 | 1/2007 | Millman et al. |
| 2007/0123848 | A1 | 5/2007 | Rioux et al. |
| 2008/0312644 | A1 | 12/2008 | Fourkas et al. |
| 2009/0287201 | A1 | 11/2009 | Lalonde et al. |
| 2010/0081577 | A1 | 4/2010 | Sidhu et al. |
| 2010/0100087 | A1 | 4/2010 | Mazzone et al. |
| 2010/0274178 | A1 | 10/2010 | LePivert |
| 2013/0103126 | A1* | 4/2013 | Harikrishna ............ A61F 7/12 607/105 |
| 2017/0151008 | A1 | 6/2017 | Mazor et al. |
| 2018/0303535 | A1 | 10/2018 | Yu et al. |

FOREIGN PATENT DOCUMENTS

| | | |
|---|---|---|
| EP | 1389447 A1 | 2/2004 |
| EP | 1430849 A1 | 6/2004 |
| EP | 2260778 A1 | 12/2010 |
| GB | 2236253 A | 4/1991 |
| WO | 2000032126 A1 | 6/2000 |
| WO | 2001087379 A2 | 11/2001 |
| WO | 2003037202 A1 | 5/2003 |
| WO | 2006009580 A2 | 1/2006 |
| WO | 2008099380 A2 | 8/2008 |
| WO | 2008157042 A1 | 12/2008 |
| WO | 2009112269 A2 | 9/2009 |
| WO | 2009137924 A1 | 11/2009 |
| WO | 2016196066 A2 | 12/2016 |
| WO | 2016196066 A3 | 12/2016 |

OTHER PUBLICATIONS

Seger M. et al., "Achieving elongated lesions employing cardiac cryoablation: A preclinical evaluation study", (2012) Cryobiology (60) Epub May 3, 2012, 6 pages.

Skanes, Allan C, et al. "Cryoablation: Potentials and Pitfalls", (2004) Review article: Cryoablation: potentials and pitfalls. J Cardiovasc Electrophysiol. Oct. 1, 2004, 7 pages.

Stuehlinger, Markus et al., (2015) CoolLoop® First: A First in Man Study to Test a Novel Circular Cryoablation System in Paroxysmal Atrial Fibrillation. Journal of Atrial Fibrillation 8 (3) Oct. 31, 2015, 6 pages.

Notice of Acceptance issued in parallel Australian Application No. 2012282473 issued on Feb. 6, 2017, 3 pages.

Office action is parallel European Application No. 12 737 266.2 issued on Jan. 19, 2017, 4 pages.

International Preliminary Report on Patentability and Written Opinion of corresponding PCT/EP2012/063847, dated Jan. 23, 2014, 9 pages.

International Search Report and Written Opinion of PCT/EP2012/063847, mailed on Oct. 23, 2012, 14 pages.

* cited by examiner

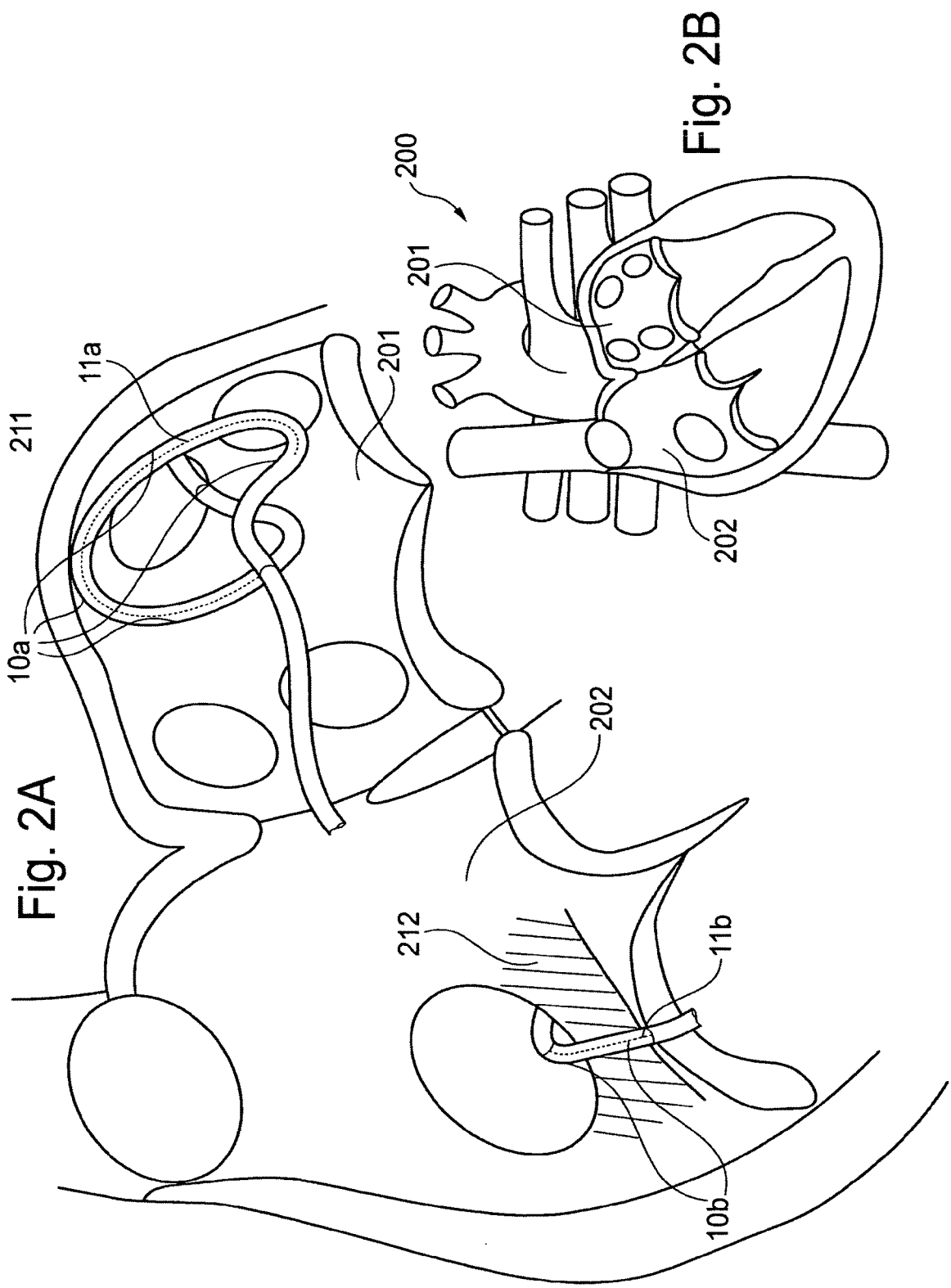

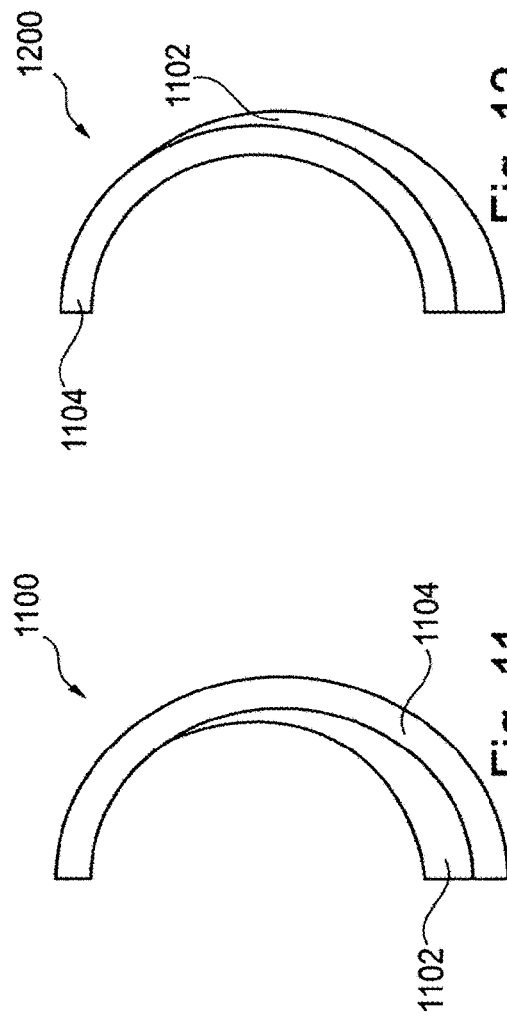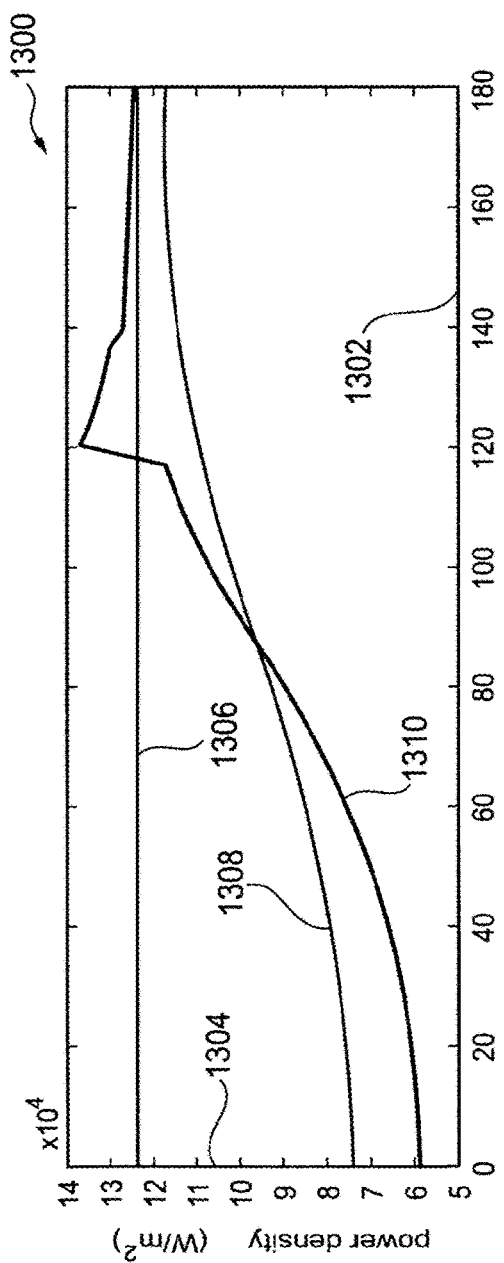

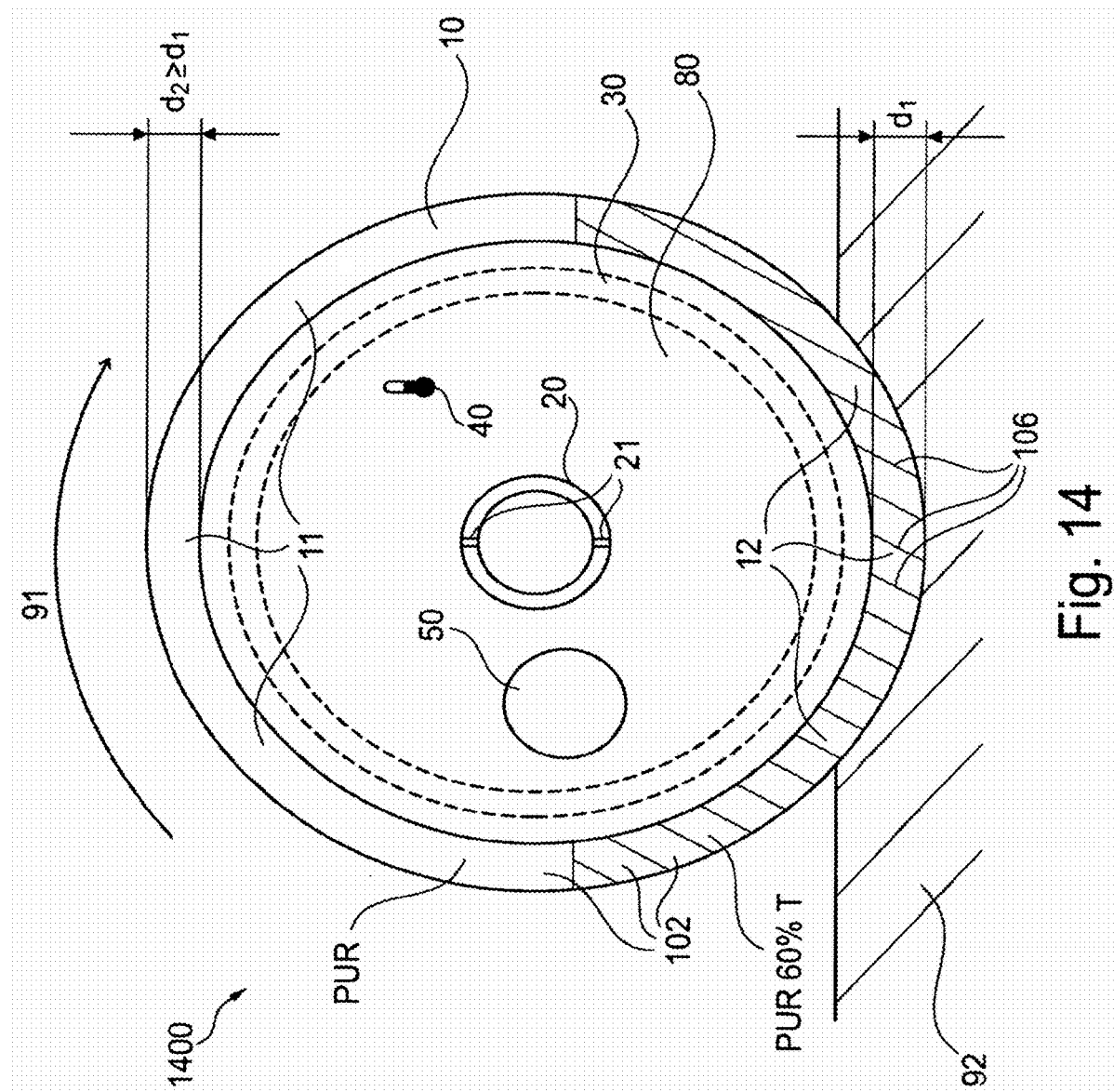

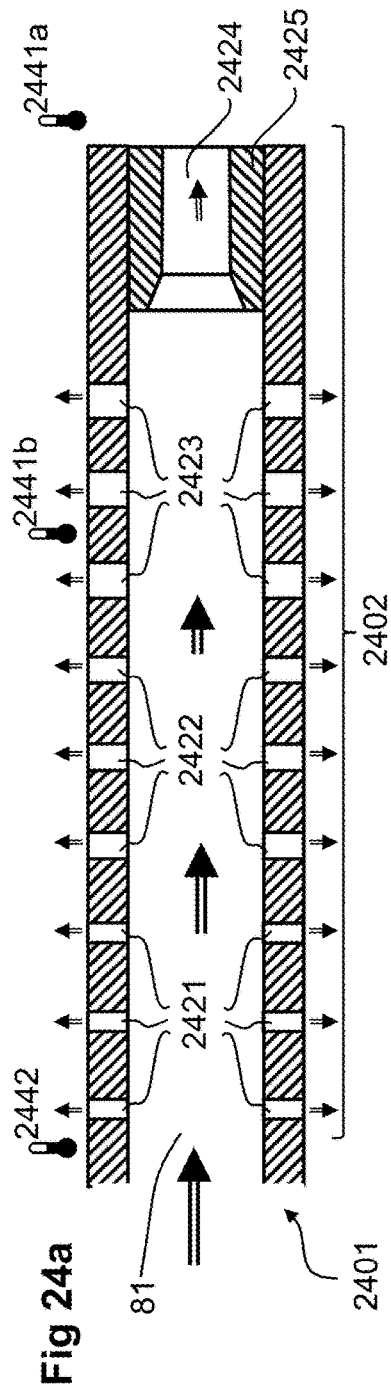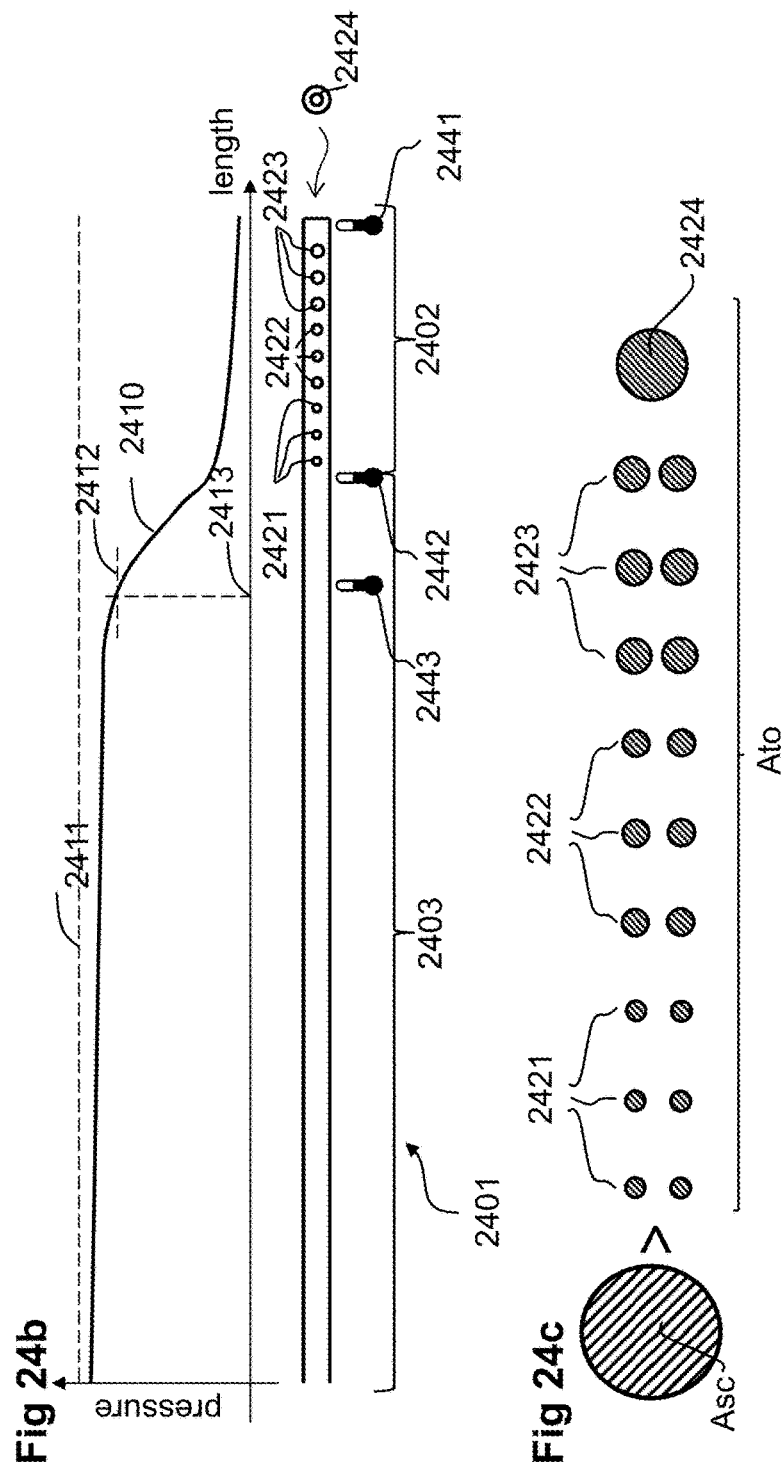

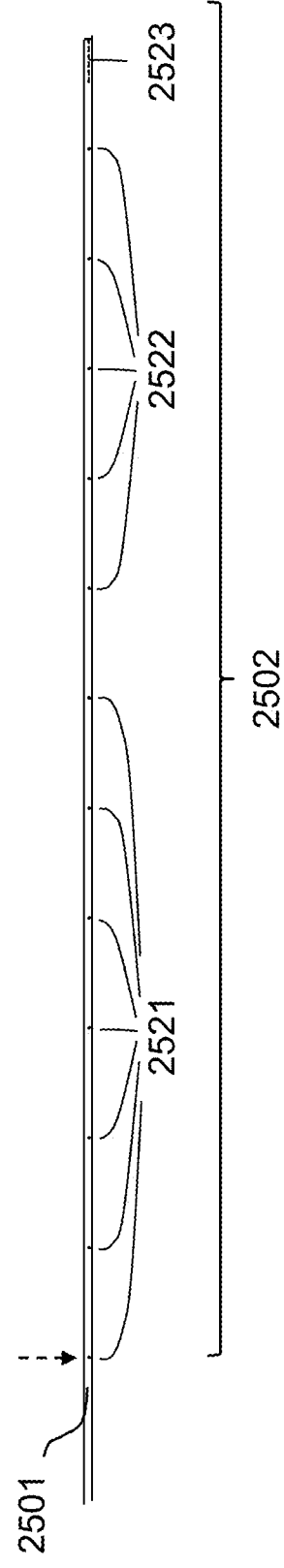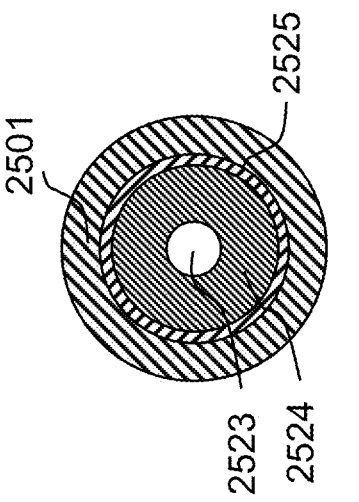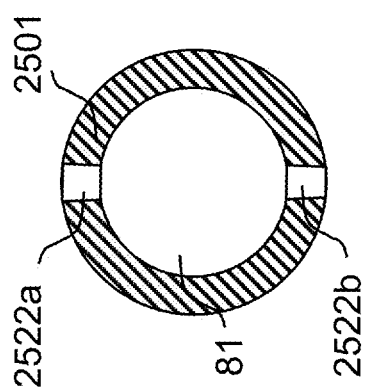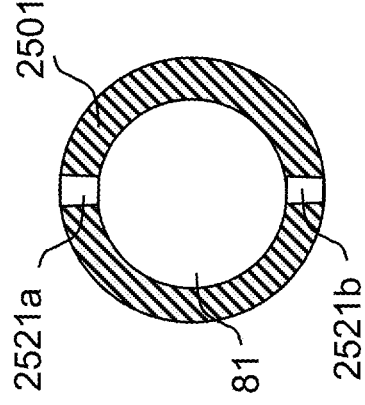

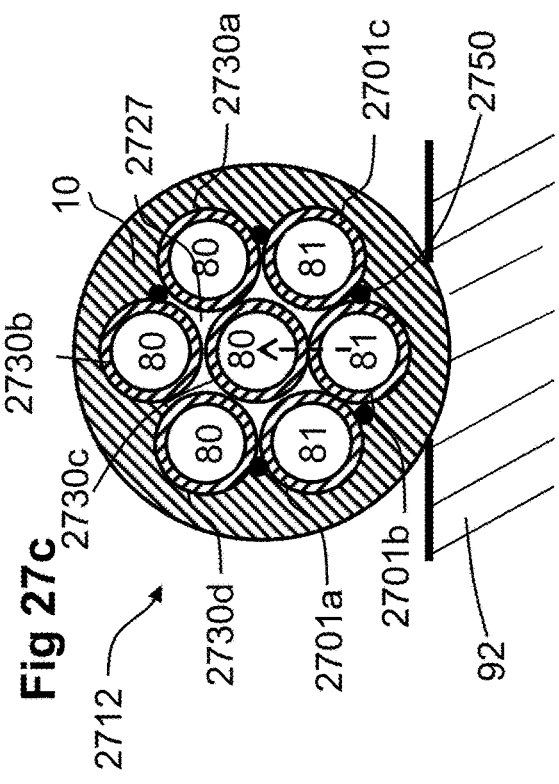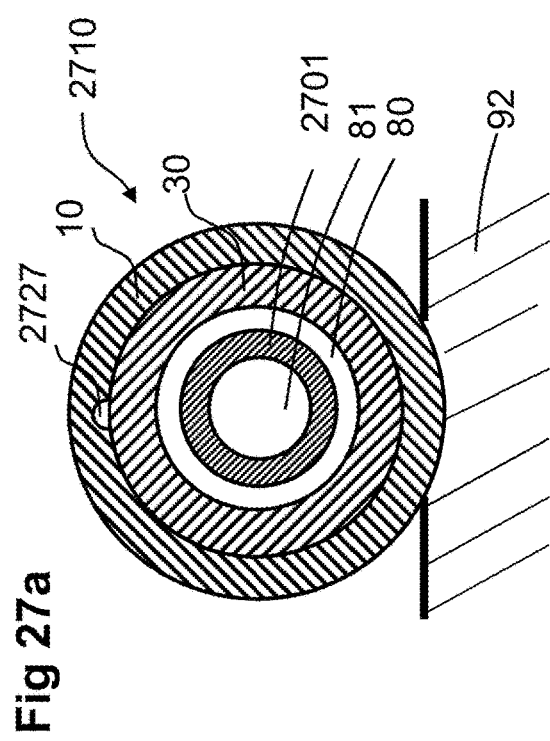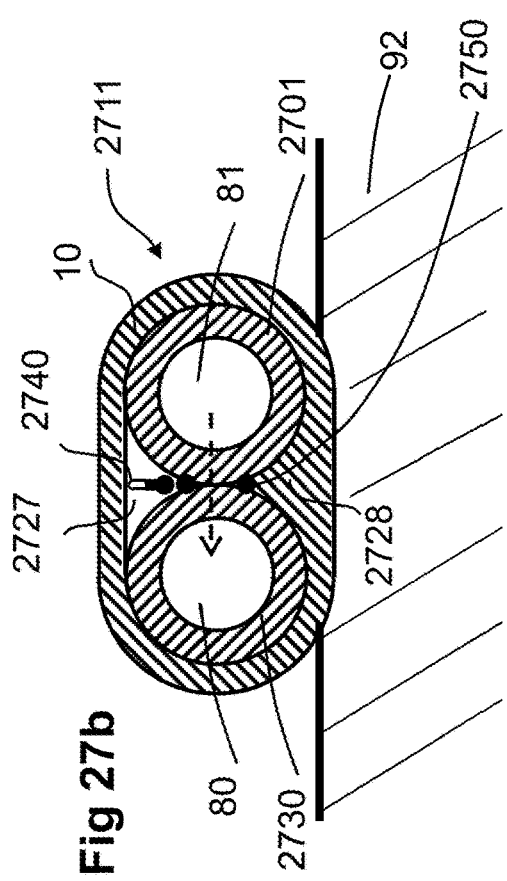

ABLATION APPLICATOR WITH A MATRIX FILLED WITH PARTICLES

CROSS-REFERENCE TO RELATED APPLICATION(S)

This application is a continuation of U.S. patent application Ser. No. 15/908,689, filed on Feb. 28, 2018, now U.S. Pat. No. 11,103,296, which is a continuation-in-part of U.S. patent application Ser. No. 14/232,886, filed Apr. 21, 2014, now U.S. Pat. No. 9,918,772, which is a National Phase Patent Application and claims priority to and the benefit of International Application No. PCT/EP2012/063847, filed on Jul. 13, 2012, which claims priority to and the benefit of European Patent Application No. 11174062.7, filed on Jul. 14, 2011, the disclosures of which are hereby incorporated by reference in their entireties.

FIELD OF THE INVENTION

The invention relates to ablation applicators.
Moreover, the invention relates to ablation devices.
Furthermore, the invention relates to ablation methods.

TECHNOLOGICAL BACKGROUND

In the field of cryoablation (therapeutic destruction of tissue by the application of extreme cold), a refrigerant vaporizes at low pressure and low temperature in a boiling chamber of an ablation catheter or a surgical probe. A thermally conductive structure forming a cryoapplicator allows the heat-exchange of the refrigerant with the tissue. Cryoablation, cryotherapy or cryosurgery are established treatments for the controlled destruction of tissue by the application of extreme cold. Examples for application are the removals of warts or moles, the destruction of tumor for the treatment of liver, prostate and lung cancer, and the selective ablation of cardiac tissue for the treatment of arrhythmia.

Rigid metallic structures are in widespread use for cryoapplicators, particularly if the target area is a spot or point like region. Here, U.S. Pat. Nos. 6,629,417 and 6,182,666 describe systems for the treatment of skin and endocervical tissue. Devices for the focal ablation of cardiac tissue are described in U.S. Pat. Nos. 5,281,213, 5,423,807 and 6,589,234. A system for cooling very small portions of tissue to extremely low temperatures is described in U.S. Pat. No. 5,901,783.

If tissue is ablated along an elongated region more flexible structures are used. Here, bellows surface can maintain both heat conduction and flexibility as described by U.S. Pat. No. 6,241,722. WO 00/32126 describes the combination of flexible segments with low thermal conduction with rigid segments of high thermal conduction. Here, also methods for the realization of a varying thermal conduction along the circumference of a cryoapplicator (good thermal conduction to the target tissue while limiting the heat loss on the opposite side of the applicator) are described. Furthermore, the use of thin walled tubing or inflatable balloon like material for the realization of good heat conduction in a flexible structure is described in U.S. Pat. No. 6,602,247 and EP 1,430,849.

One example which may require the creation of an elongated lesion in cardiac tissue is the treatment of atrial fibrillation. Here, a catheter design containing a loop like cryo-applicator structure is described in EP 1,356,779 and U.S. Pat. No. 6,979,331. Another example is the treatment of atrial flutter by creating an elongated lesion in the area of the cavotricuspid isthmus area as described in PCT/EP2009/001804.

Furthermore, WO 2009/112269 discloses an ablation element for an ablation device, the ablation element comprising a tubular body defining an inner lumen. The tubular body comprises a core formed by a wound filament structure and comprises a mantle surrounding the core. The tubular body, particularly the mantle, is configured to have a spatially varying value of thermal conductivity along a circumference of the tubular body.

However, although the arrangement of WO 2009/112269 already provides a proper solution for the spatially dependent supply of a cooling medium to tissue, there is still room for improvement.

SUMMARY OF THE INVENTION

There may be a need for an ablation applicator allowing for a spatially dependent supply of an ablation medium to surrounding tissue in an efficient way.

According to an exemplary embodiment, an ablation applicator for an ablation device is provided, the ablation applicator comprising a tubular body defining an inner lumen to which an ablation medium is conductible, wherein the tubular body comprises a matrix in (i.e. within and/or on) which a plurality of particles are accommodated (for instance are embedded in the matrix and/or are provided around the matrix).

According to another exemplary embodiment, an ablation device is provided which comprises an ablation catheter comprising an ablation applicator having the above mentioned features and being adapted to ablate physiological material, for instance material of a heart.

According to another exemplary embodiment, a method of configuring (or designing) an ablation applicator for an ablation device in accordance with at least one predefined ablation characteristic (for instance any target property which the ablation applicator to be designed should have in terms of ablating tissue) is provided, wherein the method comprises forming a tubular body defining an inner lumen to which an ablation medium is conductible and comprising a matrix in which a plurality of particles are accommodated, and selecting (for instance in terms of material selection, selection of geometrical parameters, selection of the density distribution of the particles in the matrix, etc.) the matrix and the particles so as to meet the at least one predefined ablation characteristic by the correspondingly configured ablation applicator.

According to another exemplary embodiment, an ablation method is provided, wherein the method comprises conducting an ablation medium to an inner lumen defined within a tubular body which comprises a matrix accommodating a plurality of particles, and ablating material by contacting the material with an external surface of the tubular body.

According to yet another exemplary embodiment, a cryoapplicator tubing is provided which is made from a polymer (as a matrix) being filled with particles in a first section (particularly a first circumferential section of the tubing) and being unfilled (i.e. being free of such particles) in another second section (particularly a second circumferential section of the tubing differing from the first circumferential section), wherein at least in one quarter (which may or may not be at least partially part of the first section or the second section) of a circumference of the cryoapplicator tubing, a heat transfer parameter is larger than 1500 W/m$^2$K and at least in one other quarter (which may or may not be at least partially part of the first section or the second section) of the circumference the heat transfer parameter is smaller than 1200 W/m²K. Furthermore, an ablation device having a cryoapplicator with these features is provided as well.

According to an exemplary embodiment, an ablation applicator for an ablation device for ablating tissue of a blood vessel is provided, the ablation applicator comprising a tubular body defining an inner lumen to which an ablation medium is conductible, and a control mechanism configured for converting the tubular body between a passive operation mode (wherein "passive" is meant in terms of an ablation procedure, i.e. when no ablation is carried out; an example for a passive operation mode is an elongate operation mode) for inserting the ablation applicator into the blood vessel and an active operation mode (wherein "active" is meant in terms of an ablation procedure, i.e. when ablation is carried out or is about to be carried our; an example for an active operation mode is a spiral operation mode in which the tubular body assumes a spiral-shaped configuration; another example for an active operation mode is a spread operation mode in which the tubular body may expand laterally for contacting a wall of a blood vessel) for ablating tissue of the blood vessel, for instance along a helical path (alternatively, any other continuous or discontinuous ablation path is possible). Furthermore, an ablation device having an ablation applicator with these features is provided as well.

According to yet another exemplary embodiment, an ablation method of ablating tissue of a blood vessel (for instance a kidney blood vessel), particularly of an artery or a vein, more particularly along an inner surface of an artery or a vein, is provided, wherein the method comprises inserting a tubular body of an ablation applicator in a passive operation mode (wherein "passive" is meant in terms of an ablation procedure, i.e. when no ablation is carried out; an example for a passive operation mode is an elongate operation mode) into the blood vessel, converting the tubular body from the passive operation mode into an active operation mode (wherein "active" is meant in terms of an ablation procedure, i.e. when ablation is carried out or is about to be carried our; an example for an active operation mode is a spiral operation mode) when the tubular body is located at a target position in the blood vessel, and conducting an ablation medium to an inner lumen defined in the tubular body to thereby ablate tissue of the blood vessel, for instance along a helical path (alternatively, any other continuous or discontinuous ablation path is possible), when the tubular body is in the active operation mode.

In the context of this application, the term "ablation device" may particularly denote any apparatus which is adapted to ablate, deactivate, destroy or remove material, particularly tissue of a physiological object such as a human being or an animal, via the application of an ablation medium such as extreme cold provided by a cryoablation medium.

In the context of this application, the term "ablation applicator" may particularly denote a member or a part of an ablation device at which the actual tissue ablation is carried out, particularly by icing tissue. The ablation applicator may be part of a catheter.

In the context of this application, the term "tubular body" may particularly denote a body having an inner lumen of any desired internal and external shape. In a cross-section, the internal shape and/or external shape may be circular, oval, polygonal, etc. The tubular body may for instance have a round cross section, a square cross-section, etc.

In the context of this application, the term "ablation medium" may particularly denote a fluid, particularly a cryofluid such as $N_2O$, which is configured for providing cooling power for ablation tasks. Other possible ablation media are radio-frequency current, ultra-sound, laser, etc. An object to be ablated may particularly be a human being, an animal, or any plant (any organism). More particularly, it may be an organ of such a physiological object, particularly a heart or a part thereof, for instance the isthmus. It may be a living body so that living tissue may be investigated or processed.

In the context of this application, the term "lumen" may particularly denote a material free volume within the tubing through which an ablation medium such as a refrigerant may be guided so as to cool the tubular wall of the ablation applicator.

In the context of this application, the term "matrix" may particularly denote a support structure with a continuous material property in which individual particles are to be embedded. In other words, the matrix may form a continuum in which internal spaces are filled with the particles.

In the context of this application, the term "particle" may include any physical structure in solid, liquid or gaseous matter or even vacuum circumferentially surrounded by material of the matrix. Such particles may be basically spherical, may have a cuboid shape or may even have an elongated state. The particles may be made of electrically and/or thermally conductive, semi-conductive or insulating material, may provide mechanical stiffness or flexibility and may, if desired, also have shape-memory properties. A number of particles embedded in the matrix of the ablation applicator may be larger than 10, particularly larger than 100, more particularly larger than 1.000.

In the context of this application, the term "elongate" may particularly denote that in this configuration the ablation applicator may have an oblong appearance so as to be able to move along a narrow channel such as a blood vessel. This may be a completely straight orientation of the ablation applicator, but may also be a slightly bent ablation applicator.

In the context of this application, the term "heat transfer parameter" may particularly denote the value of a parameter being defined as a ratio between a thermal conductivity (particularly, for instance in case of anisotropic thermal conduction properties, along a direction across a wall of the tubing, i.e. between an interior surface and an exterior surface of the tubing) and a wall thickness of the respective portion of the tubing between an interior wall and an exterior wall of the tubing). In this context, the thermal conductivity may be measured by the laser flash method, as for instance performed by the ZAE Bayern. In the laser flash method, a surface of a sample is irradiated with a laser beam as a heat source, and heating of an opposing surface of the sample is measured in response to the laser heating. A mathematical analysis of the time dependence of the temperature allows to determine thermal conductivity of the sample.

In the context of this application, the term "spiral" may particularly denote a helical arrangement. Such a helical arrangement may be formed by windings which are sufficiently closed together (i.e. located next to one another) that, upon application of ablation power, the thermal conductivity is sufficient to provide for a basically uninterrupted or continuous ablation along a hollow cylindrical inner surface of the blood vessel.

According to a first aspect of the invention, a matrix material having embedded therein a definable amount, kind and local distribution of particles is provided for ablation purposes to make it possible to precisely adjust the properties of the ablation to a desired application. For instance, it may be advantageous for ablation applications to have a higher thermal conductivity at specific circumferential portions (for instance those directly contacting tissue to be ablated) of the ablation applicator as compared to other circumferential portions (for instance those directly contacting tissue not to be ablated). This may be advantageous so as to apply high ablation power to tissue to be ablated, whereas other tissue should be safely parented from being cooled to a too low temperature. By embedding particles in a hollow cylindrical matrix it is also possible to adjust any other desired physical properties apart from thermal conductivity such as electrical conductivity, mechanical flexibility or stiffness, shape memory behavior, etc.

According to a second exemplary aspect of the invention, an ablation catheter is provided which is specifically configured to apply ablation energy (such as apply a cooling power) to an interior (for example tubular or basically tubular) surface of a blood vessel, particularly of a kidney. For simultaneously allowing to insert such a catheter (for instance with a basically hollow cylindrical ablation surface) into a blood vessel, it is possible to convert the active (for instance helical) shape of the ablation applicator into a passive (for instance an elongated) state in which the radial extension may be significantly reduced as compared to the active (for instance expanded) ablation mode.

DETAILED DESCRIPTION OF EXEMPLARY EMBODIMENTS

In the following, further exemplary embodiment of the ablation applicators will be explained. However, these embodiments also apply to the ablation devices and the methods.

In an embodiment, the plurality of particles comprises fibers, particularly carbon fibers, glass fibers and/or nylon fibers. The term "fibers" may particularly denote elongated pieces of a given material, for instance roughly round or rectangular in cross-section and straight or bent perpendicular thereto, optionally twisted with other fibers. Fibers may be particles which have an aspect ratio which is larger than 2, particularly larger than 5, more particularly larger than 10. The aspect ratio is the ratio between the length of the fiber (when being in or when brought to a longitudinally extending state) and a diameter of the fiber. Fibers may form networks by being interconnected or interwoven. Fibers may have a substantially cylindrical form which may however be straight, bent, kinked, or curved. Fibers may consist of a single homogenous material and may hence be a non-composite material. Alternatively, fibers may be made of different materials.

In an embodiment, the plurality of particles is aligned relative to one another in an ordered structure. Examples of such an ordered arrangement are an alignment of all particles along the same direction, but also only an angularly differing (for instance distributed) orientation of different particles however still in accordance with a preferred direction ("Vorzugsrichtung"). For instance, the particles may be extruded fibers and may then have a lower degree of ordering. Ordering the particles allows for adjusting a spatially anisotropic physical property such a thermal and/or electrical conductivity. An ordered insertion of fibers into the matrix material may allow to adjust anisotropic properties. Examples for such ordered arrangements are a straight arrangement of fibers parallel to one another and to a main extension of a tubular ablation applicator. An ordered arrangement of fibers may also result from helically winding or wrapping them around a hollow matrix tube, wherein the windings may be parallel to one another.

In an embodiment, at least a part of the plurality of particles, particularly fibers, are aligned parallel to one another, particularly aligned parallel to a longitudinal axis of the tubular body (when being in or when brought to a longitudinally extending state). For instance, in such an embodiment, heat and/or an electrical current can be transported basically along the longitudinal extension of the fibers, but not with the same efficiency to a direction perpendicularly thereto. As an alternative to a longitudinal extension, it is also possible to have a defined fiber orientation not necessarily parallel to the longitudinal axis.

In an embodiment, at least a part of the plurality of particles, particularly fibers, is spirally wound, particularly around an exterior and/or an interior surface of the tubular body. Such an arrangement may, depending on the used particles, act as a heat bridge (for promoting the conduction of heat through a wall of the tubing) or as a heat barrier (for suppressing or inhibiting the conduction of heat) through a wall of the tubing). In another embodiment, at least a part of the plurality of particles, particularly fibers, may be braided, particularly around an exterior and/or an interior surface of the tubular body. The term "braiding" may particularly denote an interweaving or twinning of two, three or more separate fibers in a diagonally overlapping pattern. The fibers may be of one or more materials. Braids can be flat or tubular. A braiding, particularly a metal braiding, may be used to provide a high mechanical stability and at the same time a sufficient flexibility.

In an embodiment, at least a part of the plurality of particles, particularly fibers, is oriented in a non-ordered way, for instance statistically or stochastically within and/or on the matrix tube. Such an embodiment may ensure that the physical properties in a section with such an arbitrary orientation of the fibers occurs is homogeneous. Hence, it is also possible to arrange the fibers in an arbitrary orientation without any preferential alignment direction, thereby allowing to adjust isotropic properties of the ablation applicator, for instance in terms of thermal conductivity.

In an embodiment, the plurality of particles comprises beads, particularly tungsten beads, silver beads, gold beads and/or barium sulphate beads. Other examples for beads include ion or ion-oxide particles for MRI contrast, or also other contrast agents (such as gadolinium). The term "beads" may particularly denote particles being significantly less elongate than fibers, for instance having an aspect ratio smaller than two, particularly smaller than 1.5. Beads may have a spherical, cuboid or other shape. Different beads may have a homogeneous or inhomogeneous shape and/or size, and may have defined or distributed shapes and/or sizes. A basically spherical geometry of such beads may ensure a corresponding homogeneity of the respective physical parameters. A spatially anisotropic geometry of such beads may ensure a corresponding inhomogeneity of the respective physical parameters.

In an embodiment, the plurality of particles comprises nanowires. The term "nanowire" may denote a wire-like structure of dimensions in the order of magnitude of several to several hundreds of nanometers (and may also cover larger or smaller dimensions). Many different types of nanowires may be used for embodiments of the invention, including semiconducting nanowires (for instance made of silicon, germanium, InP, GaN, etc.), metallic nanowires (for instance nickel, platinum, gold), and nanotubes, particularly carbon nanotubes (intrinsic or doped). The nanowire may also be an isolating nanowire (in case the nanowire is covered by an isolation layer).

In an embodiment, at least about 50% (particularly at least about 80%, more particularly at least 90%) of the plurality of particles, when being configured as beads, in the matrix have a size in a largest dimension (in case of a spatially anisotropic geometry of the particles) in a range between about 100 nm and about 100 μm, more particularly in a range between about 500 nm and about 5 μm. For instance, an average diameter of tungsten beads may be 0.8 μm.

In an embodiment, at least about 50% (particularly at least about 80%, more particularly at least 90%) of the plurality of particles, when being configured as fibers, in the matrix have a size in a largest dimension (i.e. a longitudinal direction of the fibers) in a range between about 1 mm and about 10 m, more particularly in a range between about 1 cm and about 1 m. A diameter of such fibers may be in a range between about 1 μm and about 100 μm, more particularly in a range between about 5 μm and about 20 μm. Hence, the fibers may have an aspect ratio (length divided by diameter) being significantly larger than one.

In an embodiment, the matrix is a continuum which may be free of gas inclusions such as air bubbles. Such a configuration of the matrix material is technically highly appropriate, since it ensures at the same time a sufficient stability of the ablation applicator for simplifying insertion into a living body and at the same time providing for sufficient flexibility so that the ablation applicator, when being inserted, may be guided along and around anatomic obstacles without the danger to harm or injure tissue.

In another embodiment, the matrix is formed to include at least one gas inclusion such as an air bubble. By such an intentionally provided gas inclusion, it is possible to define poorly thermally conductive sections of the tubular body.

In an embodiment, the matrix is of a material with a Shore hardness in a range between about 50D and about 70D, particularly about 55D and about 65D. Thus, a quite hard plastic (such as polyurethane) may be used for the matrix.

In an embodiment, the particles and/or the matrix material is or comprises a shape-memory material. For instance, such a shape-memory material may be configured so as to assume an initially defined geometrical shape or orientation when being heated to a certain temperature. This temperature (Af, austenite finish) at which the shape memory material converts from an initial state to a final state in terms of geometrical properties can be selected in accordance with but lower than a body temperature of a human being, for instance may be in a range between 0° C. and 20° C. Hence, insertion of a corresponding ablation applicator into the human body may automatically result in the change of the shape of the ablation applicator from an oblong state suitable for insertion into a bent or wound configuration for ablation.

In another embodiment, the ablation applicator comprises a structure of a shape-memory material provided as a member being separate from the tubing (for instance may be arranged in the lumen or in a further separate recess formed in the tubing). In such an embodiment, the shape-memory material may be adjusted separately from a matrix material so that each of these materials may be adjusted specifically in accordance with its respective function. Again, the temperature (Af, austenite finish) at which the shape memory material converts from an initial state to a final state in terms of geometrical properties can be selected in accordance with but lower than a body temperature of a human being, for instance may be in a range between 0° C. and 20° C.

In an embodiment, the matrix is made of a synthetic material, particularly a synthetic polymer such as polyurethane or silicone. Such materials have the advantage to be biocompatible, light-weight, somewhat flexible and at the same time sufficiently rigid, and also have the chemical property to allow particles to be embedded therein without losing their continuous structure. However, other polymers (such as polyamide) are suitable for this purpose as well.

In an embodiment, the plurality of particles are included in the matrix with a varying composition along a circumference of the tubular body (such as a circular perimeter in case of a hollow cylindrical tubular body). For instance, if the particles are highly thermally conductive, a high concentration or accumulation of such particles may be set at a circumferential portion of the ablation applicator at which the actual ablation or lesion should be performed. In contrast to this, the concentration of these particles may be lower in other circumferential portions of the ablation applicator which should not be subject to ablation. Even more preferably, other particles with a poor thermal conductivity may be provided with a high density in such circumferential portions of the ablation applicator which should not be subject to ablation. Therefore, the adjustment of the concentration and/or the type of the particles along a circumference may allow adjusting the ablation properties such as the ablation trajectory.

In an embodiment, the plurality of particles are included in the matrix so that the tubular body has a circumferentially varying thermal conductivity. In one more specific embodiment, a first circumferential portion has first particles with a first thermal conductivity over a first angular range, and a second circumferential portion has second particles with a second thermal conductivity over a second angular range. At least one third circumferential portion may be free of particles (i.e. may consist of matrix material) over a third angular range. The first particles may differ from the second particles, and the first thermal conductivity may differ from the second conductivity. Any of the angular ranges may be between 45° and 180°, particularly between 60° and 135°. In an embodiment in which the second particles are omitted, any of the angular ranges may be between 90° and 240°. It goes without saying that the sum of the angular ranges around the entire circumference of the tubular body is always 360°.

Additionally or alternatively, the plurality of particles are included in the matrix so that the tubular body has a longitudinally varying thermal conductivity. This may advantageous for instance in an embodiment as shown in FIG. 15 to FIG. 17 in which a tip of a catheter shall be made better thermally conducting than a remote portion of the catheter which is equivalent to a longitudinal variation of the thermal conductivity.

In an embodiment, the plurality of particles are included in the matrix so that the tubular body has a thermal conductivity within at least a part of its circumference of more than 0.25 W/(mK), particularly of more than 0.30 W/(mK). In an embodiment, the tubular body has a thermal conductivity within at least a part of its circumference of less than or equal to 1 W/(mK). If the matrix material is a kind of plastic and the particles are of high thermal conduction (for example metal or carbon) conductivities up to 4 W/mK can be obtained in the direction across the wall of the tubing i.e. from the inner surface to the outer surface by a dense packing of the particles. It has turned out that these values of the thermal conductivity are highly advantageous to provide for a precise and defined ablation.

In an embodiment, a volume percentage of the fibers in the tubular body (i.e. a ratio between the volume of the fibers on the one hand and the volume of the matrix material plus the volume of the fibers on the other hand) is in a range between about 20 vol. % and about 80 vol. %, particularly in a range between about 40 vol. % and about 70 vol. %.

In another embodiment, a mass percentage of the beads in the tubular body (i.e. a ratio between the mass of the beads on the one hand and the mass of the matrix material plus the mass of the beads on the other hand) is in a range between about 20 mass % and about 80 mass %, particularly in a range between about 40 mass % and about 70 mass %.

At lower partial volumes/masses of the particles, the effect of the particles may become too weak for high performance ablation. At higher partial volumes/masses of the particles, it may become difficult to securely embed the particles in the matrix material.

In an embodiment, the tubular body comprises a first section in which a plurality of particles of a first type are included in the matrix, and comprises a second section in which a plurality of particles of a second type are included in the matrix. By providing two or more different types of particles having different physical properties, the spatial dependency of desired thermal, geometrical, mechanical and/or electrical properties can be further refined.

In an embodiment, the tubular body comprises a third section being free of particles. Also the provision of particles only in a certain portion along the circumference may already allow to adjust the properties of the ablation applicator in a spatially dependent manner, since in the particle free portion the properties are defined by the matrix material only.

In an embodiment, the particles of the first type are thermally conductive, and the particles of the second type are thermally insulating. Hence, the thermally conductive particles should be accumulated along a definable lesion trajectory, whereas the thermally insulating particles may be located in portions of the circumference of the tubing which shall not be subject to a lesion.

In an embodiment, the tubular body comprises a first section in which the plurality of particles are included in a matrix section of a first type (for instance in a first matrix material), and comprises a second section in which the plurality of particles are included in a matrix section of a second type (for instance in a second matrix material differing from the first matrix material). Hence two, three or even more different types of matrix materials may be used to form the tubing to fine-tune the properties of the ablation applicator.

In an embodiment, the particles have a core and a coating at least partially covering the core. For example, the material of the core (such as a sphere or a cylinder) may be configured or optimized with regard to the physical properties to be achieved, whereas the coating (such as a sphere shell or a hollow cylinder) may provide compatibility with the surrounding matrix material, for instance may be optimized with regard to adhesion to the matrix material.

In an embodiment, the tubular body has a closed end formed at least partially by the matrix and the particles. In other words, a for instance hollow cylindrical section of the tubular body may be closed at one end by a half shell. The closed end may for instance have a semi-spherical shape to prevent any injury when the ablation applicator is inserted into a human being.

In an embodiment, the ablation applicator comprises at least one electrically conductive structure at an exterior surface of the closed end and being connected to or integrally formed with the tubular body. Such an electrically conductive structure may be provided integrally with the matrix having the embedded particles (which may then have electrically conductive properties) or may be a separate component (such as a metal cap). The electrically conductive structure may function as an electrode, for instance a sensor electrode or may be used for other purposes (such as ablation) as well.

In an embodiment, at least a portion of the tubular body different from the closed end, particularly an entire remaining portion of the tubular body different from the closed end, may be made of a material being free of accommodated particles. By taking this measure, specifically the closed end may function as a tip-shaped ablation applicator. It is possible to configure the accommodated particles exclusively at this tip to be highly thermally conductive. In contrast to this, the rest of the tubular body may be significantly less thermally conductive and will therefore not contribute to the ablation. Optionally, the tip may be partially or completely constituted by a metallic portion.

In an embodiment, an outer circular perimeter of the tubular body and a circular perimeter of the lumen (i.e. an inner perimeter of the tubular body) are arranged to be eccentric (i.e. not concentric) in such a manner that a thickness of the tubular body varies along the circumference of the tubular body. By taking this measure, a further design parameter (i.e. local wall thickness) for adjusting thermal conductivity between the lumen and an exterior of the ablation applicator can be provided. Usually, the thicker the material the lower is the thermal coupling.

In an embodiment, a portion of the tubular body having a higher thickness than other portions of the tubular body is filled with particles in the form of fibers aligned along a longitudinal axis of the tubular body (when the latter is in or is brought to a straight configuration). Thus, the properties of the thickened portion may be further defined by filling this region with fibers extending along a different direction than the heat flow between an interior and an exterior of the tubing.

In an embodiment, an exterior surface of the tubular body is spirally wrapped with particles in the form of fibers. Thus, after having finished manufacture of the matrix, it is possible to wind the particles simply around the external surface of the matrix tube. By taking this measure, the wrapped portion may be rendered highly or poorly thermally conductive, depending on the material of the used fibers.

In an embodiment, a thickness of the tubular body at a thinnest circumferential position of the tubular body is smaller than about 0.20 mm, particularly not smaller than about 0.16 mm. A thickness of the tubular body at other circumferential positions of the tubular body may be larger. Such a small thickness may ensure proper thermal coupling between the lumen and an exterior of the ablation applicator, for instance by the filling with appropriate thermally conductive particles. At the same time, the thickness is sufficiently large to allow sufficient stability of the ablation applicator particularly during insertion and to provide a thermal decoupling between interior and exterior of the tubing by the filling with appropriate thermally insulating particles. In an embodiment, a thickness of the tubular body at a thickest circumferential position of the tubular body is smaller than about 0.35 mm, particularly not smaller than about 0.25 mm.

In an embodiment, the tubular body is formed by inserting the plurality of particles into the matrix by pultrusion. Pultrusion is a continuous process for manufacture of composite materials. Particles such as reinforced fibers are pulled through a resin or other matrix raw material, possibly followed by a separate preforming system, and into a heated die, where the resin undergoes polymerization or the other matrix raw material is hardened. This is a very simple procedure of manufacturing the matrix with the particles embedded therein. Other methods of providing ordered arrangements of particles being ordered relative to one another and/or relative to the matrix material are wrapping fibers around a matrix tube, magnetically aligning magnetic beads by applying a magnetic field, etc.

In an embodiment, the ablation applicator comprises an ablation medium supply line for supplying ablation medium, being arranged within the lumen and having a number of recesses (for instance twelve hole pairs, but it may even be a single hole) for conducting ablation medium from the ablation medium supply line to the lumen for thermally contacting the ablation medium with the tubular body. Thus, for instance a refrigerant such as $N_2O$ may be conducted from a reservoir through the ablation medium supply line or conduit. From there, it may flow through the recess or recesses, thereby expanding into a boiling chamber which may be a volume between the ablation medium supply line and the tubular body. The cooling power of the ablation medium may then impact the tubular body with its spatially dependent thermal conductivity properties, particularly circumferentially varying thermal conductivity properties. Hence, although the boiled ablation medium is supplied to a basically hollow cylindrical space between ablation medium supply line and the tubular body, an anisotropic transmission of the cooling power to tissue surrounding the tubular body may nevertheless be adjusted, thereby allowing to select which portions of the tissue are to be ablated and which not.

In an embodiment, the number of recesses comprises recesses arranged with a predetermined spacing in the longitudinal direction of the tubular body. The predetermined spacing may preferably be less than 8 mm or even less than 6 mm, thereby assuring that ablation medium is thermally contacting with a continuous section of the tubular body.

In an embodiment, the cross-sectional area of at least one proximal recess (a recess positioned towards the proximal end of the ablation applicator) is smaller than the cross-sectional area of at least one distal recess (a recess positioned towards the distal end of the ablation applicator). Thereby, pressure variations along the ablation medium supply line can be compensated, such that a uniform distribution of the ablation medium is achieved along the tubular body.

In an embodiment, at least two neighboring recesses (two recesses separated by the predetermined spacing) may have the same cross-sectional area. In particular, several groups of recesses may be arranged in the longitudinal direction of the tubular body, wherein the recesses of each group has the same cross-sectional area.

In an embodiment, the ablation applicator may further comprise a temperature sensor arranged within the inner lumen for monitoring the temperature therein. The temperature sensor may preferably be arranged in the vicinity of one of the recesses. A further temperature sensor may preferably be arranged in the vicinity of another one of the recesses. The temperature sensor is preferably arranged towards a proximal end of the lumen (i.e. in a proximal portion of the ablation applicator) and the further temperature sensor is preferably arranged towards a distal end of the lumen (i.e. in a distal portion of the ablation applicator). Thereby, a temperature difference between the proximal and the distal end may be detected and compensated for.

In an embodiment, the ablation applicator may further comprise a shaping structure, such as a super-elastic shape memory structure, arranged within the inner lumen and adapted to provide the tubular body with a desired shape. The shaping structure preferably comprises nitinol. Further, the shaping structure preferably comprises an austenite finish temperature (Af-temperature) below 12° C., such as below 6° C. Thereby, the super- or pseudo-elastic properties can be obtained at body temperature (i.e. around 37° C.), such that the shaping structure can maintain the desired shape of the tubular body during and after insertion of the ablation applicator into a patient.

In an embodiment, the ablation device may further comprise a positioning catheter adapted to be positionable in a heart (wherein the ablation catheter and the positioning catheter may be different members being however functionally coupled to one another). However, in other embodiments, the provision of an ablation catheter alone is sufficient and a separate positioning catheter may be omitted, for instance if a mechanism is provided which triggers the ablation applicator to be converted between different shapes, for example from an insertion shape (for instance elongate) to an ablation shape (for instance helical or curved), or vice versa. Optionally, the positioning catheter may comprise a fixation mechanism (such as a balloon or a fixation helix) for fixing the positioning catheter in the heart.

The aspects defined above and further aspects of the invention are apparent from the examples of embodiment to be described hereinafter and are explained with reference to these examples of embodiment.

FIG. 2A shows a cryoapplicator in a loop-like structure for ablating tissue around a pulmonary vein ostium in the left atrium of the heart according to an exemplary embodiment of the invention.

FIG. 2B shows the anatomical conditions in a heart in which the cryoapplicator of FIG. 2A can be implemented.

FIG. 11 shows a cross-section of an ablation applicator according to another exemplary embodiment using a combination of different kinds of fibers.

FIG. 12 shows an ablation applicator according to another exemplary embodiment having another combination of different kinds of fiber.

FIG. 13 is a diagram showing the angular dependency of the cooling power flow of the ablation applicators of FIG. 11 and FIG. 12.

FIG. 14 shows a cross section of an ablation applicator for an ablation device according to an exemplary embodiment of the invention, wherein a circumferential variation of particles embedded in the matrix ensures a circumferentially varying thermal conductivity of the ablation applicator.

Figure 22:
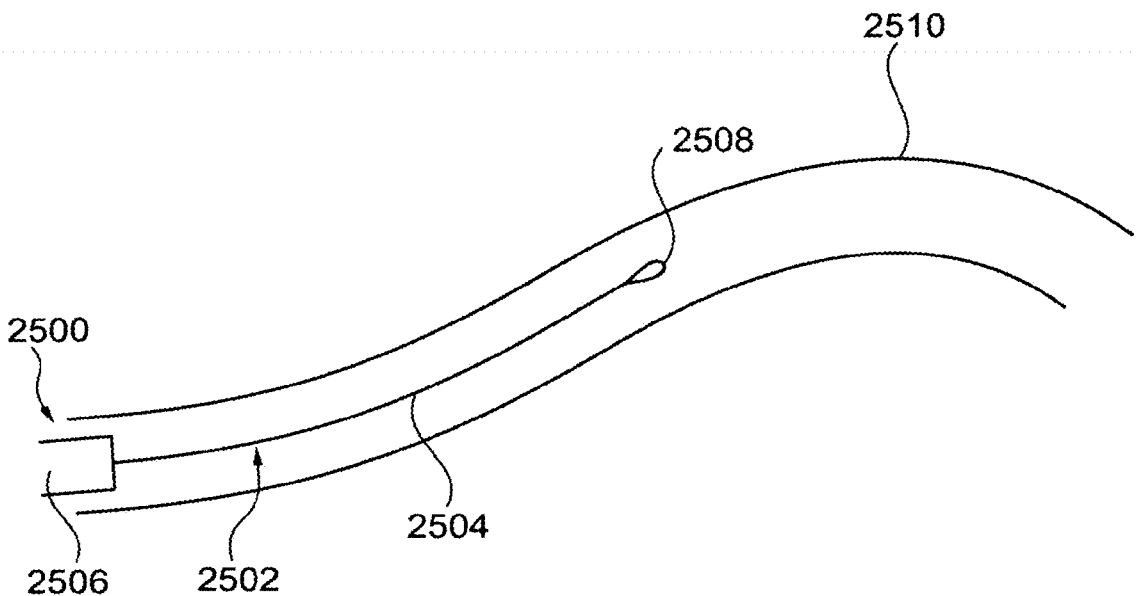
Figure 23:
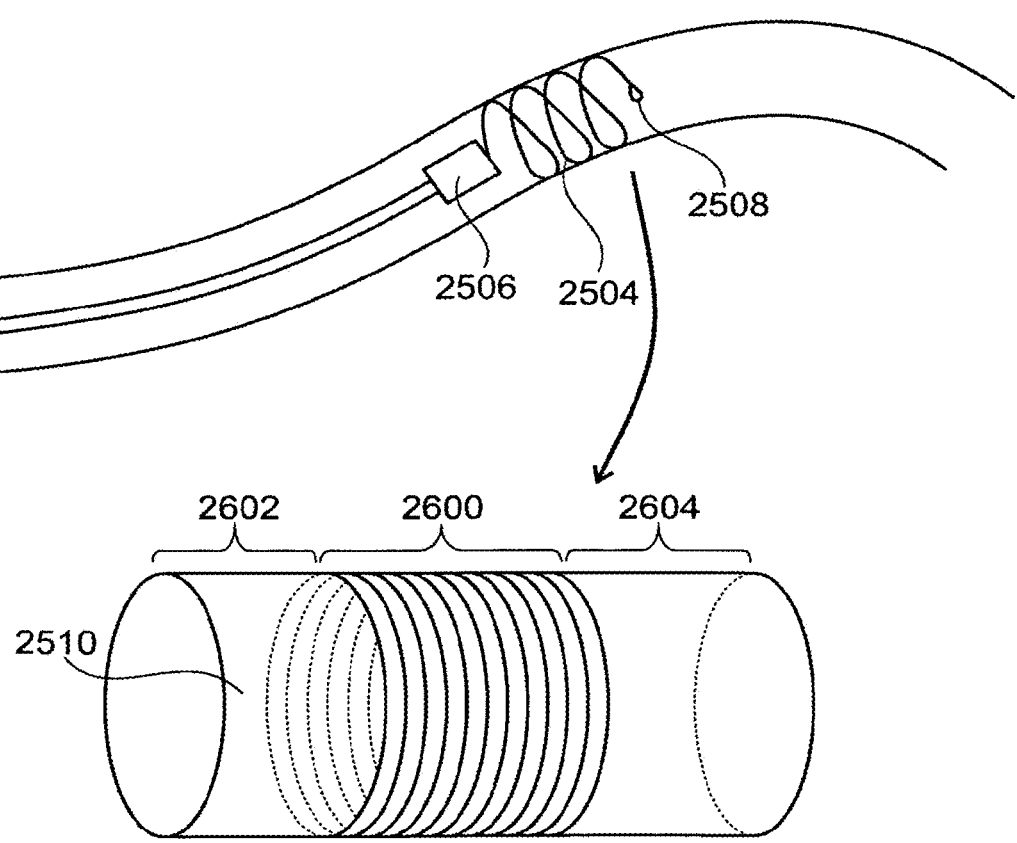

FIG. 22 and FIG. 23 schematically illustrate an ablation device according to another exemplary embodiment of the invention in which an ablation applicator can be converted from an elongated state to a helical configuration, so that in the latter configuration ablation in a artery of a kidney is possible along a basically cylindrical ablation area.

FIG. 24a shows an ablation device embodiment illustrating a schematic arrangement of refrigerant exit holes in a supply tube.

FIG. 24b is a diagram illustrating the pressure inside the supply tube along with a long axis.

FIG. 24c is a detail view of the exit holes of FIGS. 24a and 24b.

FIGS. 25a to 25e show another alternative embodiment supply tube exit hole distribution structure.

Figure 26:
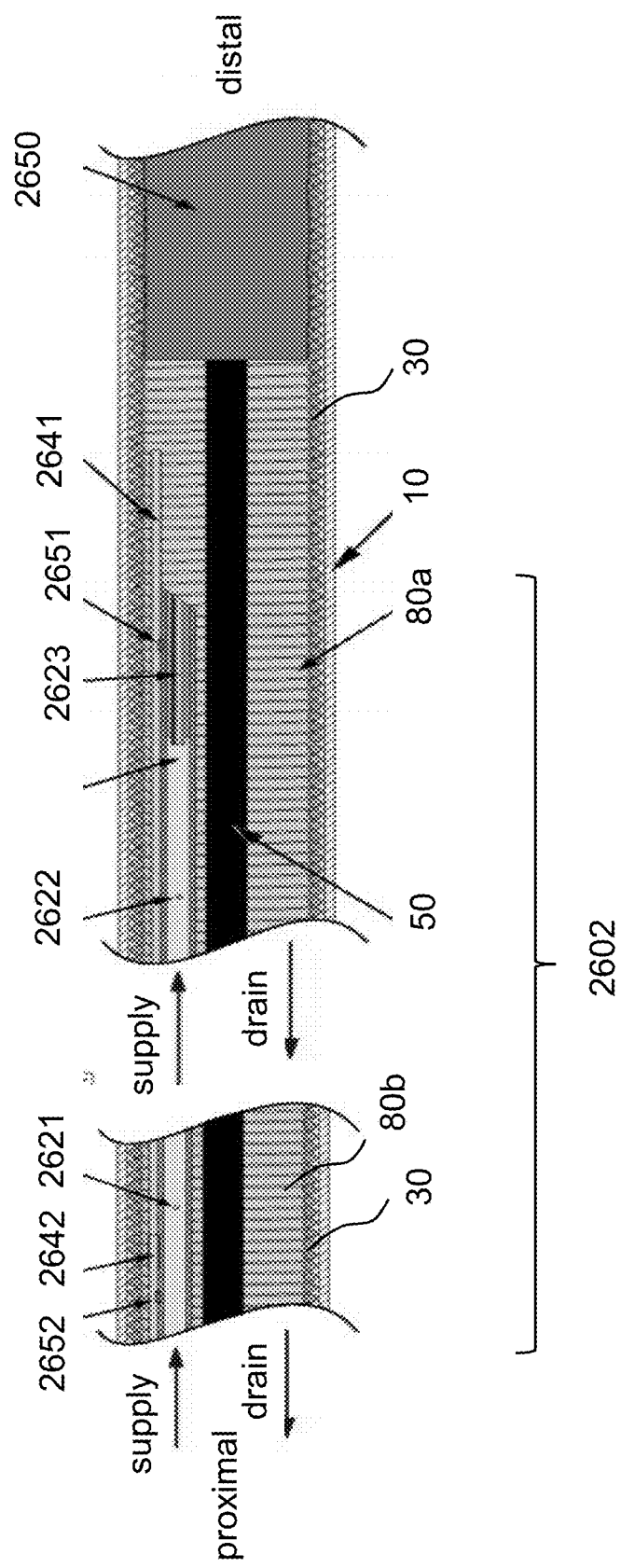

FIG. 26 shows a cross-section of a distribution structure inside a cryo-applicator along a long axis.

FIG. 27a to 27c show cross-section views of alternative embodiment cryo-applicators for creating elongated lesions.

The illustration in the drawing is schematically. In different drawings, similar or identical elements are provided with the same reference signs.

In an embodiment, a cryoapplicator with fiber-reinforced plastic is provided. Particularly, one embodiment provides a cryoapplicator tubing made from a combination of filled and unfilled polymer. At least in one quarter of the circumference the heat transfer parameter may be larger than 1500 W/m²K, and at least in one quarter of the circumference it may be smaller than 1200 W/m²K.

For the construction of cryo-applicators it may be desirable to adjust different material properties in a broad spectrum of physical parameters. For example heat conduction should be high in a portion having contact with the target tissue while in a portion opposed to the blood stream heat it should be low for avoiding undesired waste of cooling medium. Also mechanical properties may be tailored to a specific application. For example bending stiffness of an applicator should be kept low enough for moving it with ease through a curved tube (geometry of a vessel or an introducer) but high enough to span up a flexible target tissue structure (for example the atrial muscle) for ensuring sufficient mechanical contact between the applicator and the tissue. Similarly torsional stiffness can be selected above a specific value to ensure that the applicator can be rotated but additionally it may be requested that it remains also below a specific value to ensure that a desired deformation can be performed. This deformation may be needed when the applicator has to take a specific shape for the application of cryoablation. Here the material properties can be selected such that kinking is avoided. Furthermore, for increasing the functional safety of a cryoablation device, the applicator shall be pressure resistant withstanding a high burst pressure but also a vacuum condition. In certain embodiments it is possible that the material properties vary over the length of an applicator.

When metallic structures are provided for cryoapplicators they may be simultaneously used as recording electrodes for electric signals. Here a large surface may be needed for sufficient heat exchange with the tissue during cryoablation. On the other hand for a better local resolution of an electrocardiogram (ECG) recording a smaller electrically conduction may be desirable. Thus, at least a portion of the applicator shall be a thermal conductor but an electrical isolator.

Figure 1:
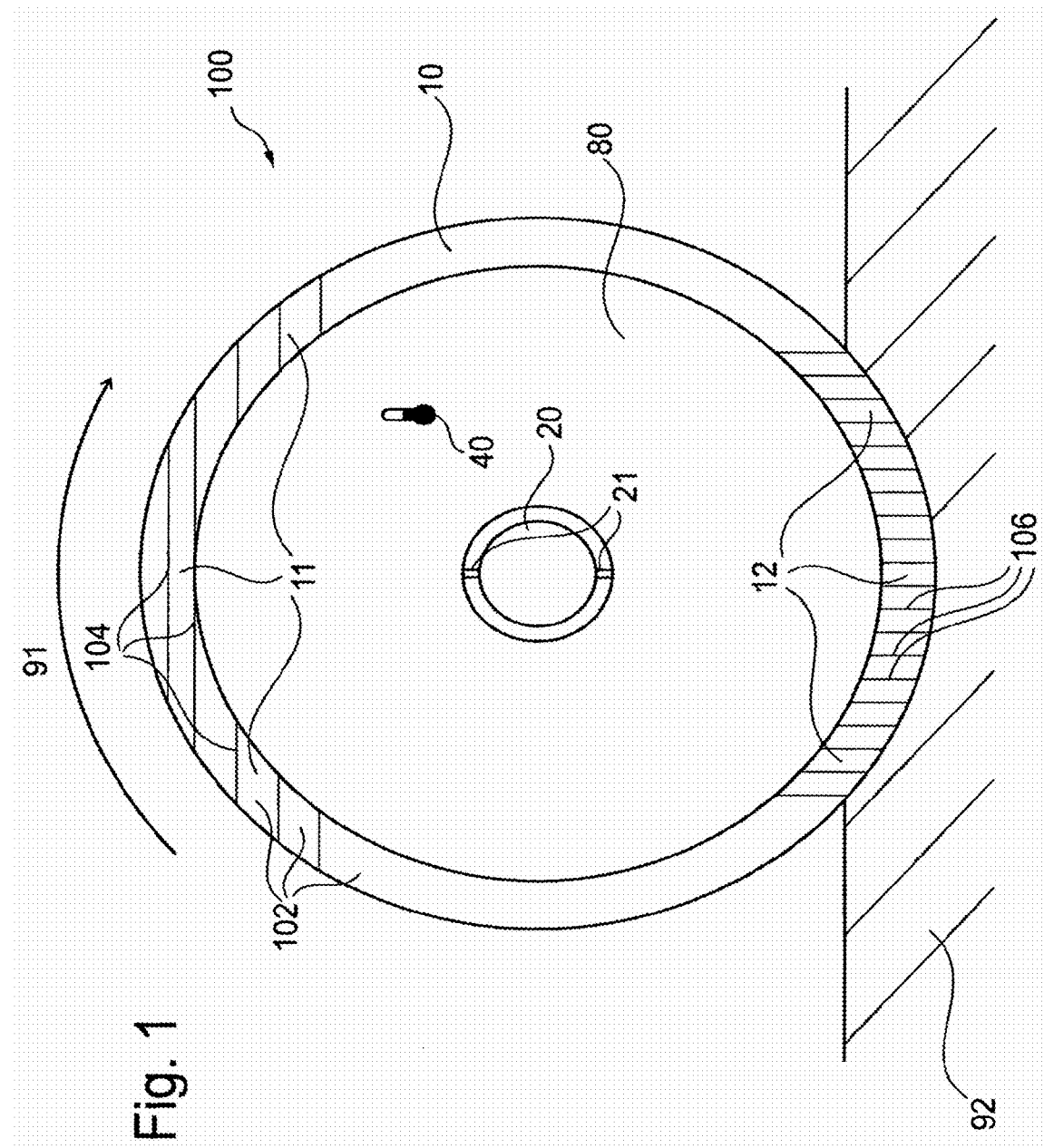
FIG. 1 is the cross-section of a cryoapplicator of a cryogenic ablation device with a circumferentially varying thermal conductivity according to an exemplary embodiment of the invention.

FIG. 1 shows a cross-section of an ablation applicator 100 for a cryogenic ablation device according to an exemplary embodiment of the invention.

The ablation applicator 100 has a tubular body 10 which may also be denoted as an outer tubing jacket and which defines a lumen functioning as a boiling chamber 80 of refrigerant supplied as an ablation medium to the ablation applicator 100. More precisely, a liquid refrigerant is supplied to an interior of a tubular ablation medium supply line 20 in a liquid form. Upon traversing a number of recesses 21 in the tubular ablation medium supply line 20, the ablation medium expands in the boiling chamber 80. Due to this expansion, a temperature reduction occurs which cools an inner surface of the tubular body 10 of the ablation applicator 100.

The tubular body 10 comprises a hollow cylindrical polymer matrix 102 in which a plurality of particles are embedded sectionwise. More precisely, in an isolating zone 11 of the tubing 10, thermally isolating particles 104, for instance in form of thermally isolating fibers or in form of thermally isolating beads, are embedded.

In contrast to this, a thermally conducting zone 12 in another circumferential portion of the tubing 10 has embedded therein second thermally conductive particles 106, for instance in the form of thermally conductive fibers or in form of thermally conductive beads.

As can be taken from the schematic drawing of FIG. 1, both the first thermally isolating particles 104 and the second thermally conductive particles 106 are embedded in the matrix 102. In other words, the matrix material 102 of polymer forms a base material in which the individual particles 104, 106 are embedded. Therefore, the thermal properties around the circumference of the tubing 10 are adjusted sectionwise by a combination of the selection of the materials of the matrix 102 and the particles 104, 106, their density distribution along the circumference of the tubing 10, and their sectionwise orientation.

Hence, a principal cross section of the cryoapplicator tubing 10 designed for the creation of elongated lesions is shown in FIG. 1. The outer jacked tubing 10 of the cryoapplicator has a kind of cylindrical shape defined by an elongated structure which is in contact with the tissue 92 essentially along a line. The cross section of the applicator (FIG. 1) has a circular or oval shape. The refrigerant supply line 20 contains the micro-holes or recesses 21 for delivering refrigerant along the active section of the cryo-applicator tubing.

One or more temperature sensors 40 (for example thermocouples, PTC or NTC-sensors) may be used for monitoring the temperature along the tubing 10. The remaining cross section forms the boiling chamber 80 which defines also the refrigerant return path. The refrigerant might be removed actively (low pressure evacuation) for preventing refrigerant exit in the case of leakage of the outer sealing of tubing 10.

For the creation of elongated lesions, multiple temperature sensors 40 may be used for monitoring ablation along a line having a length of several cm. In particular, at least one sensor in the distal portion of the cryo-applicator and one in its proximal portion may be used.

One part of the cross section is in tissue contact. Thus, a high thermal conductivity is desired in a part of the cross-section termed the conducting zone 12. This zone is indicated by a vertical hatching symbolizing an increased heat transfer from the boiling chamber 80 within the cryoapplicator to the tissue 92. Measures for increasing the heat transfer involve use of material of high thermal conductivity and/or narrow wall thickness and will be described in detail below. Opposite to the conduction zone an undesired heat exchange with the blood stream 91 takes place. Here the isolating zone 11 reduces the heat transfer. This is indicated by a horizontal hatching symbolizing blocking of the heat transfer. Measures for reducing the heat transfer involve use of material of low thermal conductivity, larger wall thickness and will be described in detail below.

The ratio a of thermal conductivity $\lambda_c$ across the cross section (essentially in radial direction in FIG. 1) and the wall thickness d yields an quantitative estimate of the heat transfer property ($a=\lambda_c/d$). The conductive zone 12 is defined such that the value a is larger than 1500 W/m²K and more particularly larger than 2000 W/m²K. In the isolating zone 11 the value a is smaller than 1200 W/m²K and more particularly smaller than 1100 W/m²K.

Note that the isolating zone 11 in FIG. 1 forms a considerable portion of the circumference of the cross-section (more than one quarter but less than three quarters and more particularly more than one third but less than two thirds).

In FIG. 2A and FIG. 2B some example embodiments illustrate how the cross section of FIG. 1 might be orientated in order to create elongated lesions in cardiac tissue.

In FIG. 2A a cryo-applicator tubing 10a forms a loop like structure for ablating tissue around a pulmonary vein ostium 211 in the left atrium 201 of the heart 200 for treating atrial fibrillation. A dashed line marks the orientation of the isolating area 11a away from the tissue.

In FIG. 2A a cryo-applicator tubing 10b is shaped along the cavo-tricuspid isthmus 212 in the right atrium 202 for treating atrial flutter. Again a dashed line marks the orientation of the isolated area 11b away from the tissue.

If the creation of a continuous lesion in cardiac tissue is desired the spacing of the refrigerant exit holes or recesses 21 within the tubing 10 (see for instance FIG. 14) may be smaller than 8 mm and more particularly smaller than 6 mm. For ensuring that a uniform distribution of the refrigerant exits along the cryo-applicator, the diameter or cross-sectional area of the recesses may vary. The cross-sectional area may be smaller for proximal recesses and larger for distal recesses in order to compensate for potential pressure variations along the refrigerant supply line. Variations in cross-section can be achieved by adjusting the diameter of an essentially circular recess or the shape of the recesses from circular to oval or elongated. The cross-sectional area may vary continuously from one recess to the next. However, also step like variations are possible with a group of neighboring recesses of essentially same area and a step like variation of the area to the next group of recesses. The total increase in area from the smallest area to the largest may be between 5% and 40% and more particularly between 10% and 25%. Typically, the diameter of the circular recesses is between 10 μm and 100 μm.

At its distal end, the refrigerant supply line might be closed. Alternatively the cross section of the distal end can be reduced by inserting a short piece of tubing with a narrow distal diameter. Typically, this diameter is not larger than 100 μm.

It may be advantageous to place the temperature sensors (e.g. thermocouples 40 in FIG. 1) next to the recesses. In this situation, they can measure the refrigerant temperature right in the area of highest heat transfer to the body. This temperature will closely correlate with the boiling chamber pressure.

Figure 4:
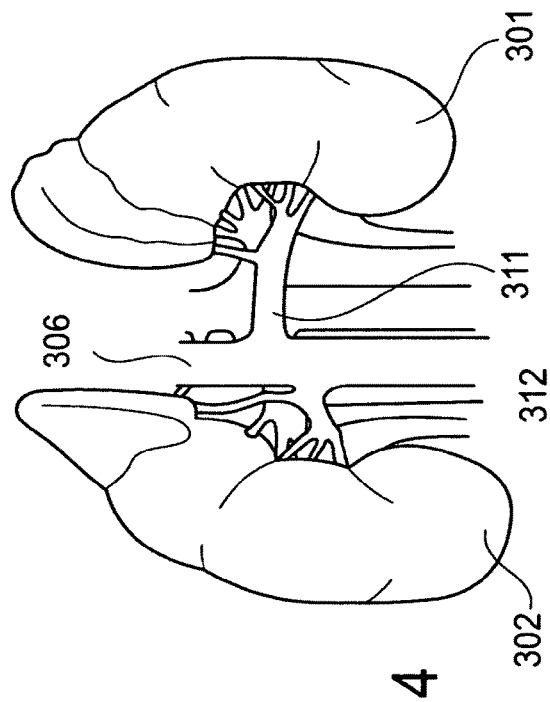
FIG. 4 shows the anatomical conditions of kidneys in which the cryoapplicator of FIG. 3 can be implemented.
Figure 3:
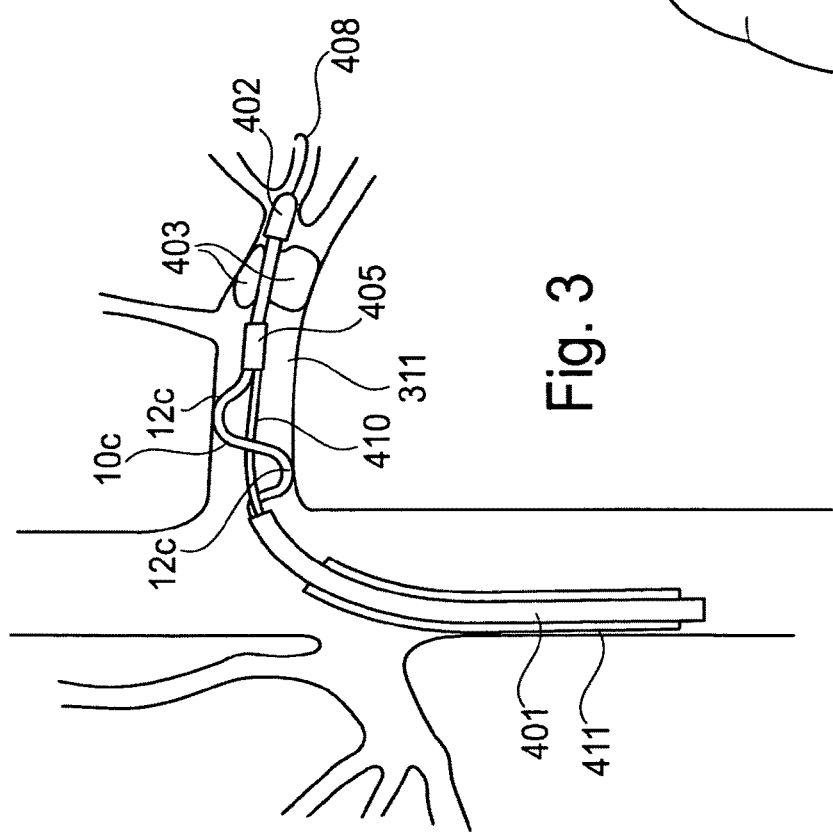
FIG. 3 shows an ablation applicator inserted for treating hypertension by neural modulation in a kidney according to an exemplary embodiment of the invention.

In FIG. 3 and FIG. 4 exemplary embodiments illustrate how the tubing 10 in FIG. 1 might be applied for treating hypertension by neural modulation. Schematically the left and right kidney 301 and 302 are depicted in FIG. 4. The left and right renal arteries 311 and 312 are carrying the blood flow from the aorta 306 to the kidneys 301, 302. In the adventitia surrounding the smooth muscle fibers of the renal arteries 311 and 312 the renal innervations are located which contribute to blood pressure control. Partial or complete ablation of these innervations can be applied for reducing blood pressure.

In FIG. 3 a helically shaped cryo-applicator 10c is inserted into the real artery for neuromodulation in treatment of hypertension. A thermally conducting zone 12c is located essentially in an outside orientation on the helical tubing such that it is in contact with the vessel wall. In two locations this is indicated exemplarily. The isolating zone is located essentially in an inside orientation of the helix such that it is directed towards the blood stream. For the shown embodiment the cryo-applicator 10c is mounted on a positioning catheter 410. This positioning catheter 410 can slide within a lumen of a catheter shaft 401 which is rigidly connected with the cryo-applicator 10c. A sheath or introducer (steerable or fixed curve) may be used for assessing the renal arteries 311. Pulling back the shaft 401 relative to the positioning catheter 410 stretches the catheter to an essentially elongated shape which allows the insertion into the body. Advancing the shaft 401 in a forward direction relative to the positioning catheter 410 triggers the formation of helical shape of the cryo-applicator 10c. The formation of this shape may be supported by a component made from a shape-memory alloy (such as component 50 in FIG. 14). For the placement of the supporting positioning catheter 410 a guide wire 408 may be used. The lumen which contains the guide wire 408 may be also used for the admission of a contrast agent which supports the visualization of the renal artery 311 in an imaging modality such as for example X-ray (particularly computed tomography, CT), MRI (magnetic resonance imaging) or ultrasonic. Alternatively or additionally a tip 402 of the positioning catheter 410 may be shaped such that it can be inserted in a branching of the vessel for increasing the stability of the positioning catheter 410. If the positioning catheter 410 should take up also pulling forces an inflatable balloon 403 may be foreseen. A sleeve 405 may provide the connection of the cryo-applicator 10c with the positioning catheter 410. In yet another embodiment a balloon 403 may be omitted and the sleeve may be integrated into the tip 402.

If the creation of a continuous helical lesion in the vessel wall is desired the spacing of the refrigerant exit holes 21 within the tubing (FIG. 14) will be smaller than 8 mm and more particularly smaller than 6 mm. If the creation of discrete point like lesions is desired in a heart the spacing will be larger than 8 mm and more particularly larger than 10 mm. In yet another embodiment the balloon 403 may be arranged proximally from the applicator. In this arrangement inflating the balloon will block the blood flow along the renal artery and, thus, decrease the thermal load during freezing.

In yet another embodiment the positioning catheter 410 is omitted. Thus by pulling back the guide wire 408 the shape memory component 50 in FIG. 14 will force the applicator 10c to take its helical shape. This embodiment may contribute to reducing the inner diameter of the sheath 411 which may be of advantage for narrow vessels. Furthermore, no mechanism is needed for moving the positioning catheter and shaft relative to each other which may contribute to a simpler and cheaper catheter design.

In yet another embodiment the guide wire 408 is omitted. The positioning catheter 410 (which may be steerable or may be not steerable but controlled by the sheath 411) is used to access the vessel. The cryo-applicator is brought from its passive stretched configuration to its active helical configuration by moving positioning catheter and applicator relative to each other.

In yet another embodiment both positioning catheter 410 and guide wire 408 are omitted. The transition from passive to active configuration is solely triggered by an shape-memory component 50 when moving the cryo-applicator 10c out of the sheath 411. This can be accomplished by pulling back the sheath or by advancing the cryo-applicator 10c.

In yet another embodiment the active configuration of the cryo-applicator 10c is not a helix but an arc-like geometry which ensures sufficient wall contact with the vessel.

FIG. 5 shows again a tubular body 10 together with a volume element or voxel V. Detailed illustrations of the constitution of the volume V in three different embodiments are shown in FIG. 6 to FIG. 8.

Figure 6:
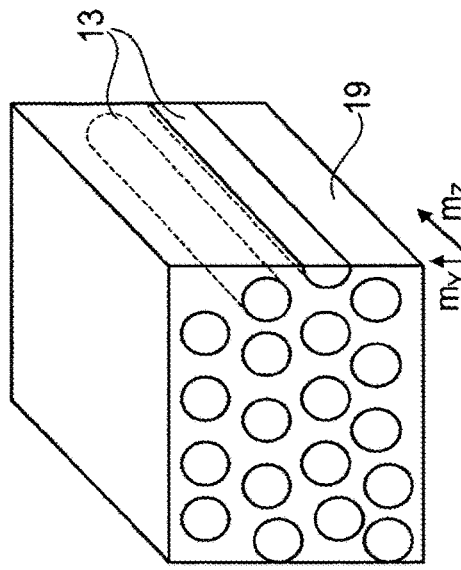
FIG. 6 to FIG. 8 show examples illustrating constitution of a voxel of the tubular body of FIG. 5 according to different exemplary embodiments of the invention, wherein in each case a polymeric matrix material is filled with particles of a polymeric or non-polymeric filling material.

According to FIG. 6, elongate fibers 13 having a high aspect ratio are aligned in a matrix 19 parallel to one another and parallel to a symmetry axis 500 of the tubing 10.

Figure 7:
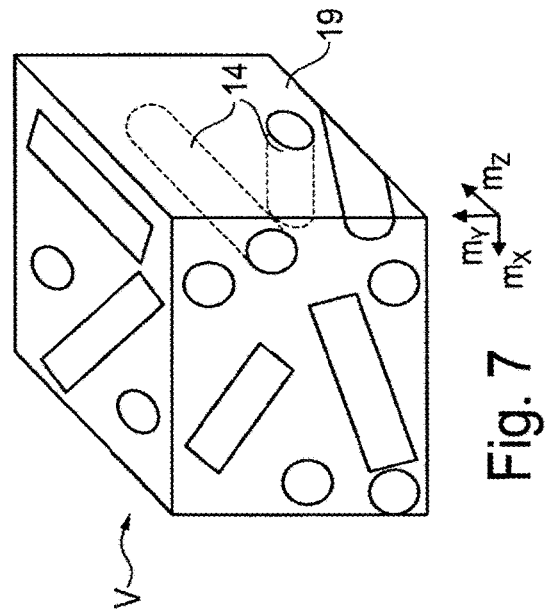

In the embodiment of FIG. 7, fibers 14 are aligned isotropically, i.e. without any orientation along a preferred direction, thereby resulting in isotropic heat transfer properties.

Figure 8:
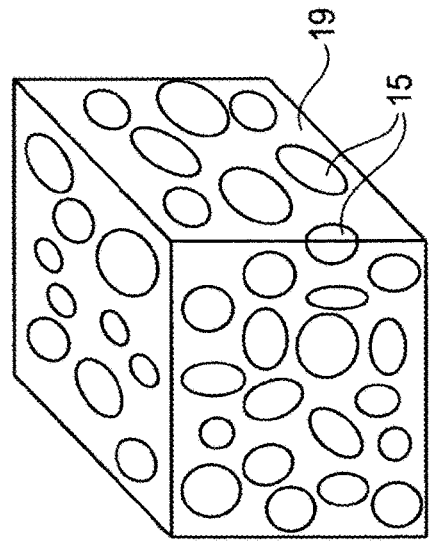

In FIG. 8 the volume V comprises again material of the matrix 19 in which bead-like particles 15 with an oval cross section are embedded.

Figure 5:
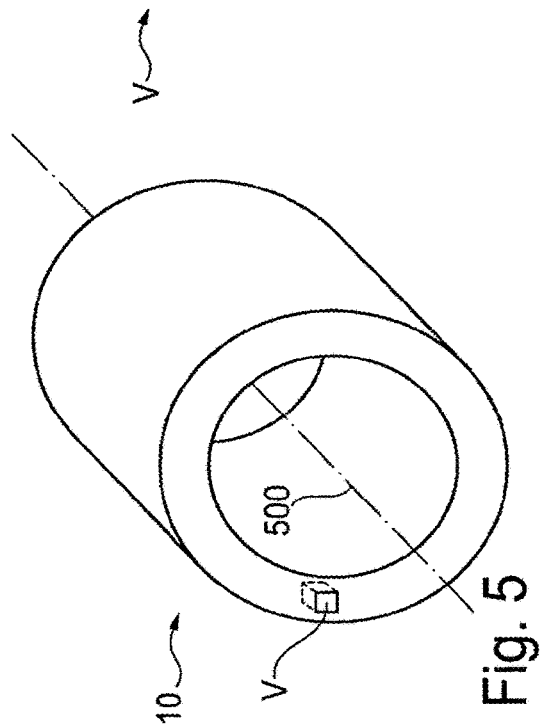
FIG. 5 shows a tubular body of an ablation applicator according to an exemplary embodiment of the invention.

Hence, in FIG. 5 to FIG. 8 example embodiments of filled polymers in the context of the present invention are described. FIG. 5 shows a piece of a cryoapplicator tubing 10 with a volume V which may be composed of polymeric matrix material filled with a polymeric or non-polymeric filling material. The filling material may be arranged in long, orientated fibers 13 (FIG. 6), in short not-orientated fibers 14 (FIG. 7) or in small particles 15 (FIG. 8). Here, fibers are essentially cylindrical structures with narrow cross sections (below 50 μm maximal diameter and more specifically below 25 μm maximal diameter) which can be long (more than a few millimeters of length) or short (less than a few millimeters of length). Long fibers 13 (FIG. 6) may be arranged by production techniques in a controllable fashion (for example pultrusion of fibers 13 and matrix material 19) such that they may be arranged essentially in parallel to the axis 500 of cryo-applicator tubing 10 or may be wound around the circumference of an applicator tubing in a defined angle. Here, from a macroscopic point of view anisotropic material properties along and across to fiber orientation may be defined. The term macroscopic may be understood such that cubic volume V contains a plurality of filling elements 13, 14 or 15 such that average material properties can be defined over the spatial extension of volume V. Exemplarily an anisotropic macroscopic material property (which can be for example thermal conductivity) is indicated by arrows $m_x$, $m_y$, $m_z$. In contrast, short fibers may be introduced within the material without control of orientation (for example extrusion of a polymeric granulate with short fibers) resulting in a pattern of randomly orientated or non-orientated fibers 14. In this case macroscopic material properties are essentially isotropic ($m_x \approx m_y \approx m_z$). Similar the filling material might be composed of particles such as beads 15 (see FIG. 8, filling elements of essentially oval shape with a maximal spatial extent below 50 μm and more specifically below 25 μm). Here, again orientation of the filling material is not controlled during production and the macroscopic material properties are essentially isotropic ($m_x \approx m_y \approx m_z$).

The relative filling volume is the ratio of the volume within tubing 10 occupied by the filling material 13, 14 or 15 and the entire volume of the tubing 10. The relative filling volume may be a value below 80%.

The matrix material 19 used for embodiments described in FIG. 6 to FIG. 8 is a polymeric material which should provide a dense and leakage proof connection between the particles or filling elements (fibers 13, 14 or beads 15). The polymer shall ensure a continuous connection between filling elements such that macroscopic material properties $m_x$, $m_y$, $m_z$ obtained are a weighted mean of matrix and filling element property. For example when pulling a tubing 10 along its major axis stretching of the material may be governed by a macroscopic (weighted average) elastic modulus which is defined by the material properties of matrix and filling material, the relative filling volume and fiber orientation in case of orientated fibers. Thus, the matrix material provides an essentially force fit connection from fiber to fiber ensuring that a mechanical load is distributed over the matrix and the filling material. Similarly, if a temperature gradient is applied across a macroscopic portion of a filled tubing (i.e. a portion several times larger than the maximum fiber diameter or maximal particle size) heat flow will be governed by a macroscopic (weighted average) thermal conductivity which is defined by the material properties of matrix and filling material and the relative filling volume. Additionally in the case of orientated fibers macroscopic conductivity will be a tensor with a different value along and across fiber orientation. Examples of matrix materials for the embodiments described above are polyurethane, silicone or polyamide. However, also other polymeric matrix materials may be used. Generally, the use of an electrically non conductive matrix material will result in a high resistive compound material. If a conductive filling material is used the compound material may conduct high frequency alternating due to capacity effects. Electrically conducting polymers with an electrically conducting filling material may be used for designing compound materials with a desired electrical resistance in the direct current range.

Referring back to FIG. 6, orientated fibers 13 may be foreseen for alternating thermal and mechanical material parameters in an anisotropic fashion. For example, carbon or metallic fibers (for example silver) may be used to increase the thermal conductivity of the material (along and to a smaller degree across fiber orientation) simultaneously with mechanical robustness (particularly tensile strength in fiber direction). For increasing mechanical robustness without or with a relatively small increase of thermal conductivity fiber materials such as nylon, glass or Teflon (polytetrafluoroethylene, PTFE) might be used. Glass fibers will result in a relatively stiff compound material along fiber direction while nylon fibers may allow the design of a more flexible compound material.

Adjustable essentially isotropic material properties may be obtained by the embodiments described in FIG. 7 and FIG. 8. For example short not orientated carbon fibers in a polymer matrix may be applied for designing a mechanically relatively stiff compound material, with a high thermal conductivity but low electrical conductivity. Metallic particles (for example Tungsten or silver) in a polymeric matrix may also result in a high thermal conductivity at a low electrical conductivity but will result in a mechanical softer material.

Note that the interface between the matrix and filling material can severely affect the macroscopically observed material properties. If the matrix material does not or purely coat the filling material, tiny gaps in the compound material may occur. This might be used to decrease thermal conductivities.

For a high thermal conductivity, a good coating of the filling material by the matrix material is essential. This can be achieved by surface treatment of the filling material or by proper selection of the matrix material. For example, the polyurethane with the brand name Textin displays a good coating with tungsten. In contrast, polyurethane with the brand name Pellethane poorly coats tungsten.

Thus, by properly selecting matrix and filling material physical parameters of the compound material can be adjusted in a wide range. Thermal, mechanical and electric macroscopic parameters may be tailored separately. Furthermore, macroscopic material properties may be chosen in an isotropic or anisotropic way.

In Table 1 some values are listed which enable the computation of the heat transfer coefficient (above denoted as "a") for some examples of fiber reinforced polymers. These values are obtained from a finite element model of composite material. This model considers the idealized situation that no polluting inclusions (air bubbles, surface coating, etc.) are present in the matrix. Thus, they are an estimate of a the highest obtainable conductivities.

TABLE 1

Conductivity values composite materials

| material matrix | conductivity matrix [W/mK] | material fibre | conductivity fibre [W/mK] | volume % fibre | conductivity along fibre [W/mK] | conductivity across fibre [W/mK] |
|---|---|---|---|---|---|---|
| silicone | 0.16 | carbon | 17 | 40% | 6.90 | 0.41 |
| silicone | 0.16 | carbon | 17 | 45% | 7.74 | 0.47 |
| silicone | 0.16 | carbon | 17 | 50% | 8.58 | 0.55 |
| silicone | 0.16 | carbon | 17 | 55% | 9.42 | 0.65 |
| silicone | 0.16 | carbon | 17 | 65% | 10.26 | 0.77 |
| silicone | 0.16 | carbon | 17 | 70% | 11.11 | 0.94 |
| silicone | 0.16 | quartz | 1.38 | 40% | 0.65 | 0.31 |
| silicone | 0.16 | quartz | 1.38 | 45% | 0.71 | 0.34 |
| silicone | 0.16 | quartz | 1.38 | 50% | 0.77 | 0.38 |
| silicone | 0.16 | quartz | 1.38 | 55% | 0.83 | 0.42 |
| silicone | 0.16 | quartz | 1.38 | 65% | 0.89 | 0.46 |
| silicone | 0.16 | quartz | 1.38 | 70% | 0.95 | 0.51 |
| silicone | 0.16 | nylon | 0.2 | 50% | 0.18 | 0.17 |
| PUR | 0.18 | nylon | 0.2 | 60% | 0.19 | 0.19 |

Using silicone as a matrix material with orientated carbon fibers at a fiber volume ratio of 60% a conductivity of 10.7 W/mK is obtained along the fibers and $\lambda_c$=0.65 W/mK across the fibers. As fiber orientation is parallel to the tubing $\lambda_c$ must be applied for the computation of the heat transfer coefficient. For a wall thickness of d=0.18 mm a value $a_{FRP}$=3610 W/m²K is obtained for the conducting area which is above the desired values listed above. Adding an isolating layer made from the matrix material silicone (thermal conductivity 0.16 W/mK) of 0.11 mm thickness a heat transfer coefficient of $a_{Matrix}$=1450 W/m²K is obtained for the isolating layer. However, in the isolating region the fiber reinforced tubing and the isolating layer are thermally in series and the total heat transfer parameter of the isolating layer is $a_{iso}$=1/(1/$a_{Matrix}$+1/$a_{FRP}$)=1035 W/m²K. This value is below the desired values listed above.

Figure 9:
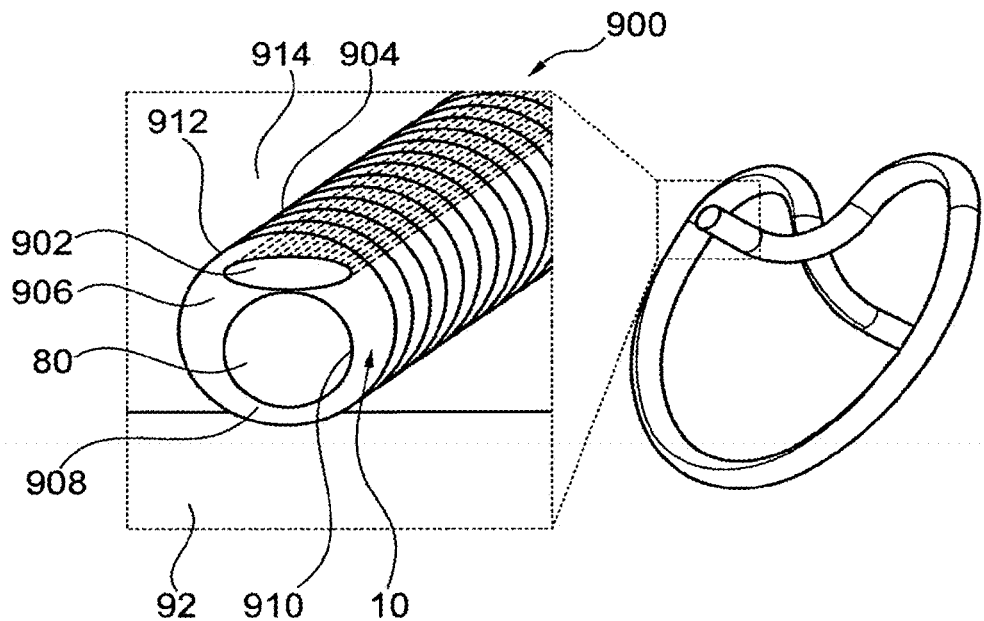
FIG. 9 shows a three-dimensional image of a portion of a loop-like ablation applicator in which various measures are taken for circumferentially varying the thermal conductivity by a combination of matrix material and a spatially varying distribution of different kinds of fibers.

In FIG. 9, an ablation applicator 900 according to another exemplary embodiment of the invention is described. FIG. 9 shows a three-dimensional view of a cross-section of such an ablation applicator 900 as well as an overview of the entire ablation applicator 900 being configured similar as in FIG. 2A. Again, for ablation, it is necessary to transfer cooling power from boiling chamber 80 to surrounding tissue 92. It is further noted that, as indicated with reference number 914, an upper portion of the tubing 10 is surrounded by blood. It is mentioned that the interior of the boiling chamber 80 is not shown in detail in FIG. 9 and can be configured for instance in a way as it is shown in FIG. 1. The tubular body 10 comprises also in this embodiment a matrix of polymer material and a plurality of particles accommodated therein. First particles are fibers 902 which extend along a longitudinal access of the tubular body 10. They are also called 0° fibers. Furthermore, so-called 90°-fibers are provided as second particles in the form of fibers 904 circumferentially wound in a helical way around an outer cylindrical surface of the tubular body 10. As a result of this arrangement, a thermally isolating zone 906 is formed in a region where the 0° fibers 902 extend. Additionally, the wall thickness of the tubular body 10 is here larger compared to other sections which further renders heat transfer inefficient in this region. On the other hand, in a cooling zone 908, the thickness of the tubular body 10 is small so that a proper heat transfer is possible in this section. It can also be taken from FIG. 9 that the surface 910 delimiting the inner lumen on the one hand and the outer surface of the tubular body 10 on the other hand shown in reference number 912 are eccentric. This also contributes to the anisotropic thermal conductivity properties of the ablation applicator 900. A structure as occupied by the fibers 902 can be manufactured by pultrusion, filament winding, pullwinding, braiding, or extrusion, for instance.

Figure 10:
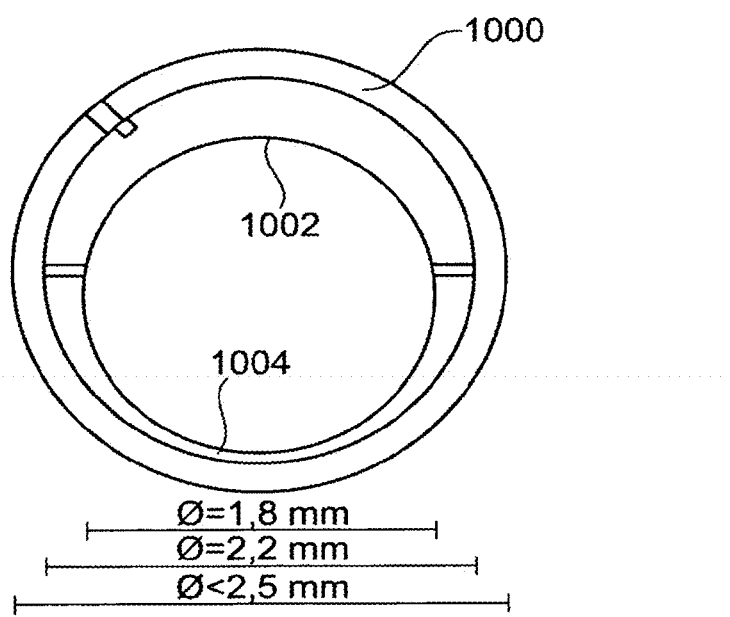
FIG. 10 shows a cross-section of an ablation applicator according to an exemplary embodiment of the invention with a circumferentially varying thermal conductivity obtained by a combination of a spatially varying matrix material and particles accommodated therein and thereon.

FIG. 10 shows a cross-sectional view of an ablation applicator according to an embodiment of the invention in which different zones of fibers can be distinguished. Carbon fibers 1000 are circumferentially or helically wound around a core which consists of an upper half circle of nylon fibers 1002 and a lower half of carbon fibers 1004. The orientation of the fibers shown in FIG. 10 is longitudinal, i.e. perpendicular to the paper plane of FIG. 10. The thickness of the wall of the ablation applicator of FIG. 10 is circumferentially varying which also contributes to the circumferential variation of the thermal conductivity.

FIG. 11 shows another cross-section of an ablation applicator 1100 according to an exemplary embodiment of the invention. In this case, quartz fibers 1102 are provided along an inner portion of the ablation applicator 1100 with a spatially dependent thickness. A tubing from carbon fibers 1104 is provided to form an outer circumference of the ablation applicator 1100 and has a thickness which is homogeneous.

FIG. 12 shows an ablation applicator 1100 according to another exemplary embodiment in which the carbon fibers 1104 form the inner portion of the tubing 1200, whereas the quartz fibers 1102 with the circumferentially varying thickness are provided to form the outer circumference of the tubing 1200.

In the embodiments of FIG. 11 and FIG. 12, the quartz fibers 1102 provide an insulating layer, whereas the carbon fibers 1104 provide a thermally conductive layer.

FIG. 13 shows a diagram 1300 having an abscissa 1302 along which a circumferential angle is plotted. Along an ordinate 1304 a power density of transferred cooling power per area is plotted. A first curve 1306 relates to a scenario in which no isolation layer 1102 is foreseen at all. A second curve 1308 relates to the scenario of FIG. 11 with an inner isolation layer 1102. A third curve 1310 relates to the scenario of FIG. 12 with the isolation layer 1102 at the outer circumference of tubing 1200.

The assessment of the heat transfer parameter yields only an estimation of the heat transfer across a wall as it does not consider the spatial arrangement of the layers. For example, FIG. 11 to FIG. 13 compare the heat flow of two embodiments computed by a finite element simulation. In FIG. 11 the isolating layer 1102 is inside the tubing, while in FIG. 12 the isolating layer 1102 is outside. It is assumed that in the tubing carbon fibers 1104 are included which are orientated in an essentially azimuthal direction (winding of fibers around the longitudinal winding of the tubing). As can be seen from the heat flux density (FIG. 13) on the outer circumference (computed by finite element analysis), arranging the isolating layer 1102 outside results in a more effective separation of thermally conducting and isolating zone as this design avoids heat transfer around the isolating zone guided along the fibers in the polymeric structure.

In some embodiments, a thin coating may be applied on the outer surface of the applicator for ensuring biocompatibility. Also, in some embodiments a leak-proof layer may be applied to the inner surface for avoiding that refrigerant enters the potential tiny gaps between the fibers and the matrix material. Also such layers contribute to the heat transfer parameter as a structure which is thermally in series with other layers.

FIG. 14 shows an application applicator 1400 according to another exemplary embodiment of the invention which is similar to the embodiment of FIG. 1. However, in contrast to the embodiment of FIG. 1, thermally isolating particles 104 are omitted. The matrix is formed of polyurethane in the shown embodiment. Furthermore, tungsten particles 106 are embedded in a lower section in order to provide for a strong thermal coupling to the tissue 92.

In the shown embodiment, it may be desirable to avoid the use of spatially well orientated fibrous structures but to add a filling material of small pieces of not orientated fibers or even particles to adjust the material parameters such that essentially isotropic macroscopic properties are obtained. For increasing thermal conductivity for example short not orientated carbon or glass fibers or particles or metallic particles (tungsten) may be added to the polymer matrix material, as illustrated by reference numeral 106 in FIG. 14. Such structures can be produced by standard methods such as extrusion. In one embodiment, small tungsten particles are added such that the tubing material contains 40 mass percent of tungsten. In addition to altering thermal conductivity, the filling material may simultaneously change other physical properties, such as X-ray (particularly computed tomography, CT), MRI (magnetic resonance imaging) or ultrasonic contrast in a desired fashion. Thus the user is able to verify if the conduction side is attached to the tissue by X-ray inspection. If for example the polymer matrix is polyurethane with a thermal conductivity of about 0.2 W/mK, adding up to 60 mass percent tungsten will increase thermal conductivity to about 0.3 W/mK. In other words, only the half of the tubing which is in contact with tissue contains the tungsten particles. This material modification in combination with a modest reduction of wall thickness increases the heat transfer parameter to a value larger than 1500 W/m²K in one section of the ablation applicator. In the remaining half, no tungsten is included and a modest increase of wall thickness is foreseen to decrease the heat transfer parameter to a value smaller than 1200 W/m²K in another section. The different appearance of these two sides in X-ray or computed tomography may help an operator to position the ablation device.

In FIG. 14, a corresponding exemplary embodiment is shown where the realization of a thermally conducting region 12 (in contact with the tissue 92) and isolating region 11 is obtained by varying wall thickness together with the filling material. In the conducting region 12, for a wall thickness of 0.16 mm and polyurethane (PUR) with 60% tungsten filling a heat transfer parameter $a_c$=1875 W/m²K is obtained. In the isolating region 11 without filling and a wall thickness of 0.2 mm a heat transfer parameter $a_i$=1000 W/m²K is obtained.

A support structure 30 like a helical coil or a wire-framework may be inserted to protect the tubing from kinking. A superelastic shape memory structure 50 may be inserted for giving the cryo-applicator a desired shape.

Nitinol may be used for obtaining super- or pseudo-elastic material properties at body temperature. When using nitinol in combination with cryo-application, it may be of advantage if the phase change of metallic structure from the elastic austenite phase to the martensite phase occurs at low temperatures. In particular, the active austenite finish temperature of the material might be adjusted below 12° C. and more particularly below 6° C. Chrome doted nitinol might be used in combination with proper heat treatment for obtaining the desired low Af-temperatures.

For ensuring mechanical stability of the desired shape, the superelastic material should be selected such that its loading and unloading plateau in the stress-curve is high. In particular, the loading plateau should be above 450 MPa at body temperature, and the unloading plateau should be above 180 MPa (again at body temperature).

In another embodiment the refrigerant supply is made from a superelastic tube (for example nitinol tube with an active Af temperature well below body temperature) combining the function of components 20 and 50 in one component. In yet another embodiment, the wire-frame 30 is made from a shape-set superelastic material combining two functions in one embodiment.

Figure 15:
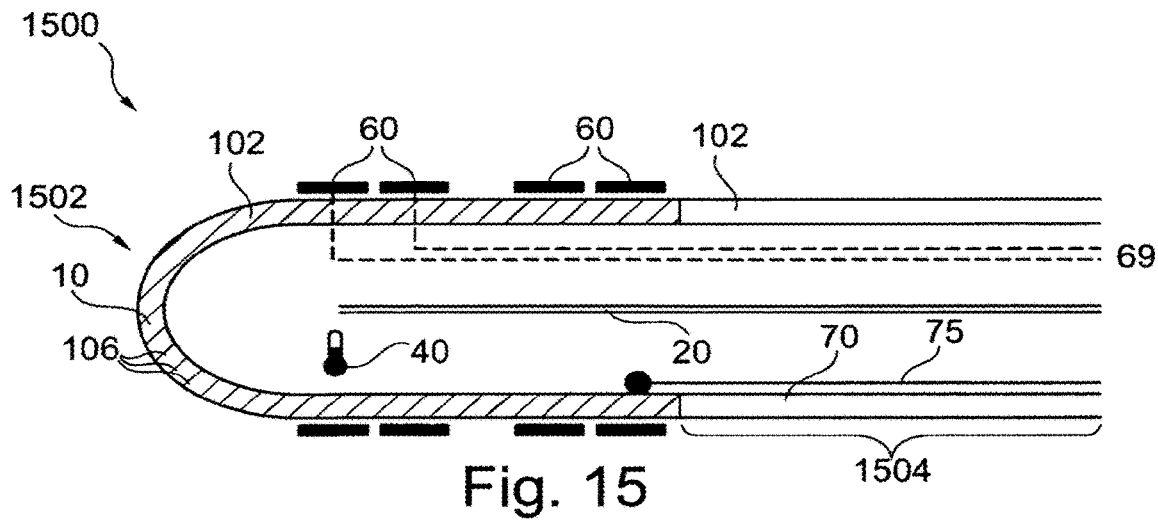
FIG. 15 to FIG. 17 show ablation applicators of ablation devices according to exemplary embodiments of the invention in which selectively a tip at a closed end of a tubular body is rendered highly thermally conductive by embedding particles in a polymer matrix, wherein a remainder of the tubular body is thermally insulating in view of the absence of particles in these remaining sections.
Figure 16:
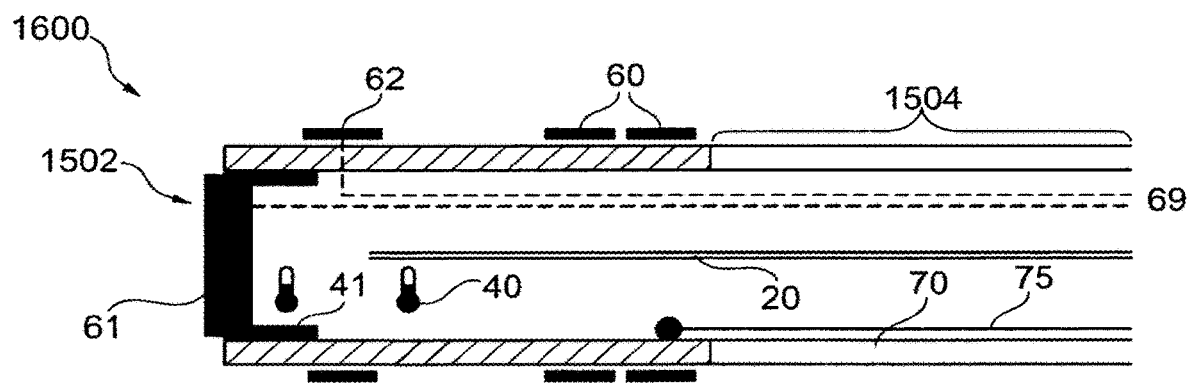
Figure 17:
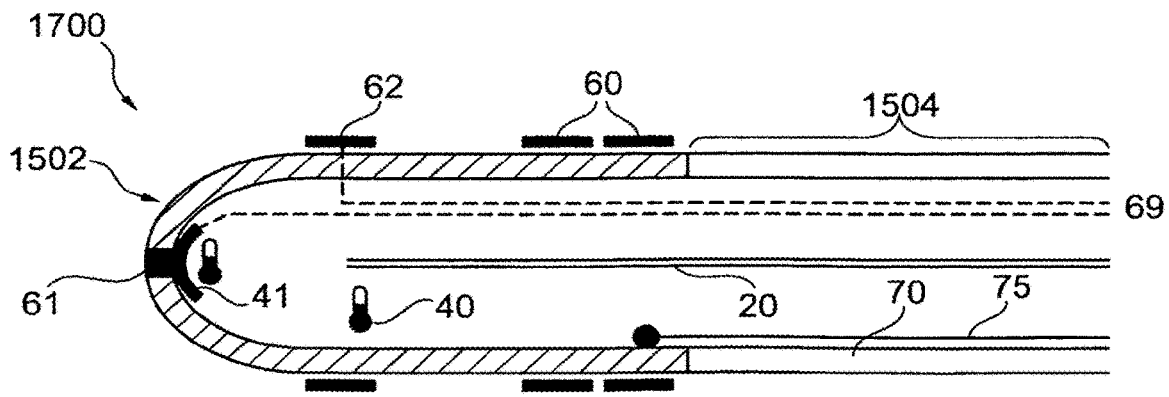

FIG. 15, FIG. 16 and FIG. 17 show ablation applicators 1500, 1600 and 1700, respectively, according to exemplary embodiments of the invention. All these three embodiments have in common that the tubular body in this case has a cupola-shaped closed end 1502 forming a rounded tip of the tubular body. As can be taken from FIG. 15 to FIG. 17, only the closed end 1502 includes filling particles in the form of thermally conductive particles 106 embedded in the matrix material 102. Thus, only the end section 1502 of the ablation application 1500, 1600 and 1700 is thermally conductive, whereas a rear portion 1504 is thermally insulating. In other words, in the rear portion 1504 the tubular body only consists of matrix material which has a poor thermally conductivity in the present embodiment.

It should be said as well that in the embodiments of FIG. 16 and FIG. 17, front portions of the tip 1502 are partially formed by metallic material, see reference numerals 61, 41. In view of its proper thermal connectivity, also this metallic material may contribute to the thermal conduction. Therefore, in each of the embodiments of FIG. 15 to 17 a cool tip is provided, i.e. a closed end 1502 with locally increased thermal conductivity. Therefore, ablation of a tip like section of tissue (not shown in FIG. 15 to FIG. 17) is possible with these embodiments.

In some applications the treatment of small, essentially focal tissue structures might be of interest. For example for the ablation of cardiac arrhythmia the elimination of conduction across a Kent bundle (Wolff-Parkinson-White syndrome) may be the target. The spatial extension of a Kent bundle is in the order of up to a few millimeters. During ablation therapy its location within the heart may be identified by analyzing the intracardiac electrogram waveform recorded on the tip of the ablation catheter (fusion of atrial and ventricular signal marks the Kent bundle). Cryoablation catheters may have a metallic tip of 5 mm to 10 mm length for providing sufficient contact surface for heat exchange with the tissue. Here the metallic tip may act simultaneously as a recording electrode and boiling chamber for the refrigerant. However, for recording local electric activity the spatial extension of the electrode should be small while for successful cryotherapy a relatively large spatial extension is needed. Here fiber reinforced polymers or polymers filled with thermally conductive compounds may be used according to exemplary embodiments of the invention for providing thermal conduction while providing electrical isolation.

FIG. 15 shows a corresponding exemplary embodiment. The boiling chamber 80 is surrounded by a filled polymeric structure 10 with a filling material increasing thermal conductivity and providing a tissue contact surface sufficiently large for cryotherapy. The filled polymeric structure may be a polymeric matrix material with short not orientated fiber segments forming a material of increased macroscopically isotropic thermal conduction and a relatively high stiffness comparable to metallic structures. On this boiling chamber 80, ring electrodes 60 are attached of comparable size to standard radio frequency (RF) ablation catheters allowing for identical spatial resolution in ECG recordings compared to RF ablation. For the distal electrode pair, electric wires 69 are shown exemplarily. The thermally conducting tip 10 is connected to a shaft 70 applying any know technique like gluing, screwing or welding. Note that in this embodiment no separation between a thermally conducting and isolating structure is made as due to the small tip size sufficient refrigerant flow can be provided even without a distinct isolating region. However, in some embodiments a separation in a thermally conducting and isolating region may be applied. A pull wire 75 can be foreseen for making the catheter tip deflectable.

In FIG. 16 yet another embodiment is shown with a distinct tip electrode 61 forming the distal closure of the boiling chamber 80. Here, combining electrodes 61 and 62 an even better spatial resolution at the distal tip compared to RF catheters can be obtained. Note that still most of the heat flow to the tissue will be conducted by the electrically isolating boiling chamber 80. In this situation semi-finished parts such as tubes can be used for constructing the cryoapplicator (boiling chamber housing) 10 which may reduce the cost for production. The distal electrode 61 can be fixed in the boiling chamber by any know fixing mechanism such as gluing, screwing, etc.

Alternatively or additionally, a tip forming procedure can be used for bringing the polymer into the desired shape, see FIG. 17, and for providing force fit and leak-proof attachment of the boiling chamber housing 10 with the distal electrode 61. At the proximal end of the boiling chamber polymer welding can be applied for a force fit and leak-proof attachment of boiling chamber 10 and catheter shaft 70. However, also any other known fixation technique can be applied.

Figure 18:
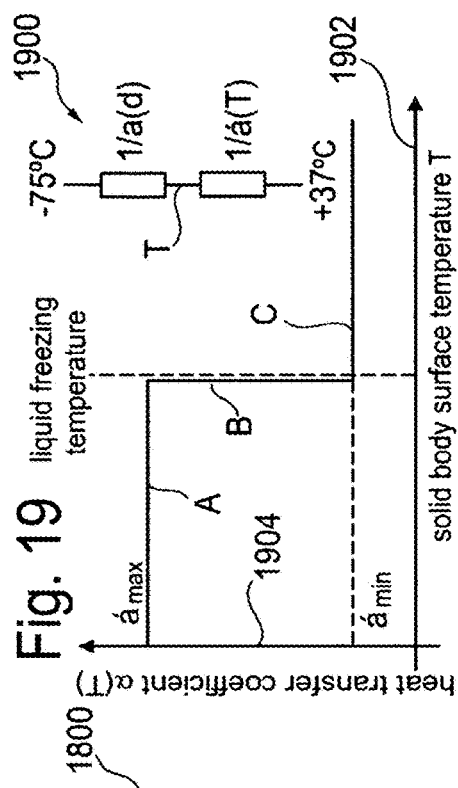
FIG. 18 is a diagram illustrating a dependency between the temperature at an ablation applicator and the time as obtained experimentally and by computer simulation.
Figure 19:
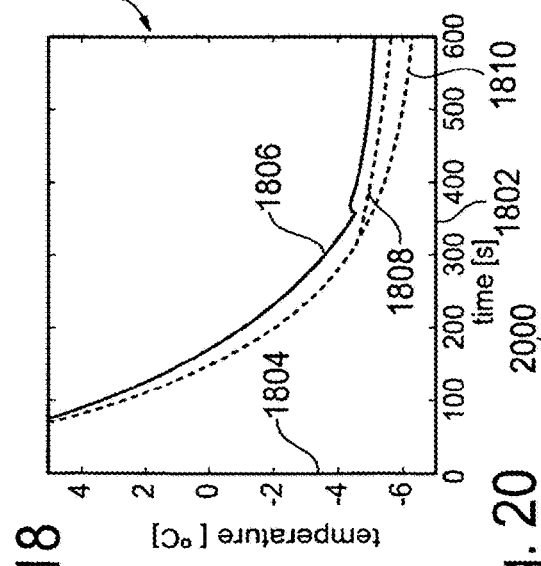
FIG. 19 illustrates the dependency between a heat transfer coefficient and a solid body surface temperature.

FIG. 18 illustrates a diagram 1800 having an abscissa 1802 along which the time is plotted. Along an ordinate 1804 the temperature is plotted. A first curve 1806 relates to measurement data, whereas a second curve 1808 relates to a first computer simulation and a third curve 1810 relates to a second computer simulation FIG. 19 plots a diagram 1900 having an abscissa 1902 along which the solid body surface temperature is plotted. Along an ordinate 1904 a heat transfer coefficient is plotted. The curve shown in diagram 1900 corresponds to the dashed trace 1808 in FIG. 18.

Figure 20:
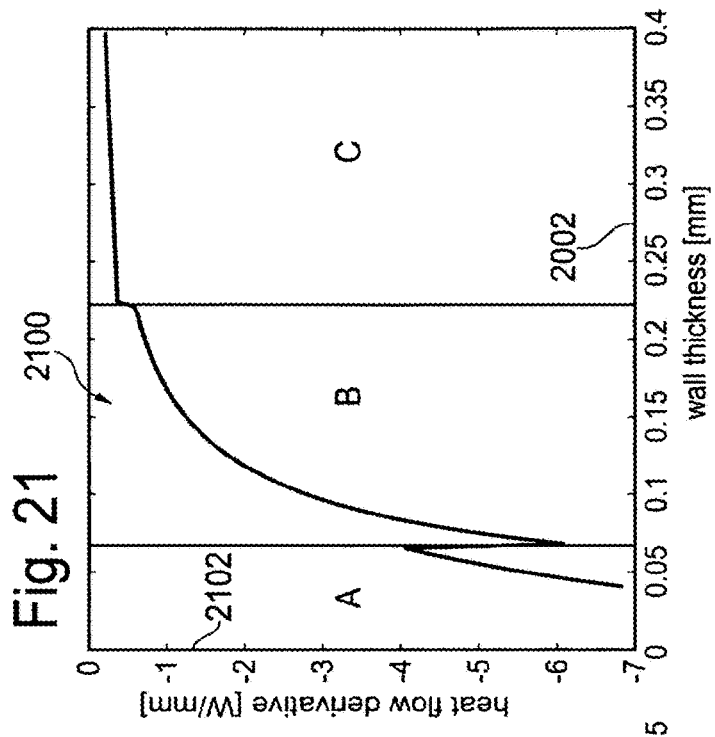
FIG. 20 shows a diagram illustrating the dependency between a calculated heat flow and a wall thickness of an ablation applicator according to an exemplary embodiment of the invention.

FIG. 20 illustrates a diagram 2000 having an abscissa 2002 along with a wall thickness of tubing is plotted. Along an ordinate 2004 a heat flow is plotted. In the diagram 2000, three sections A, B and C are distinguished which can also be seen in FIG. 19.

Figure 21:
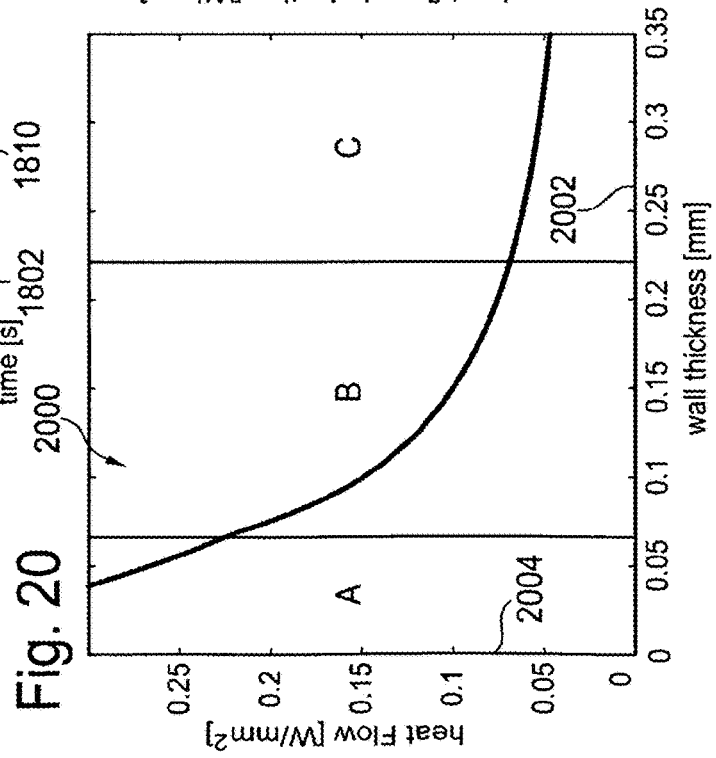
FIG. 21 shows a diagram illustrating the dependency between a derivative of the heat flow and a wall thickness of an ablation applicator according to an exemplary embodiment of the invention.

FIG. 21 illustrates a diagram 2100 which has the same abscissa 2002 as the diagram 2000. Along an ordinate 2102 the derivative of the heat flow is plotted which shows meaningful features particularly at borders between sections A and B and between sections B and C, respectively.

FIG. 18 to FIG. 21 illustrate the model underlying the thermal dimensioning of the thermally isolating region (and conductive region) in the context of embodiments of the present invention. It is assumed that the worst case thermal load imposed on the cryo-applicator is due to blood stream. Dimensioning is based on the assumption that the heat transfer coefficient ($a$) between a solid body and a liquid increases substantially when the surface temperature of the solid body drops below the freezing temperature of the liquid.

This assumption is supported by experimental data shown in FIG. 18. A metallic surface is cooled in a water bath by a thermoelectric cooler. The measured temperature is indicated by the first curve 1806. A sharp bend can be observed in the measured temperature trace when surface temperature drops by about five degrees below the freezing point of water. This measurement data is compared with two computer simulations, see second and third curves 1808, 1810. In one model (dashed trace, second curve 1808) a step like change of the heat transfer coefficient is assumed at −4.6° C. as indicated in FIG. 19. This model can reproduce the sharp bend in the trace. If in contrast the heat transfer coefficient is assumed to be constant no bend can be observed.

Without being bound to a specific theory the inventors have recognized that the heat transfer to a liquid medium can be reduced by avoiding that the solid body surface temperature drops below the freezing point of the medium. In other words, a thermal isolation is effective when beginning ice formation on the applicator surface is avoided in circulating blood. This can be quantitatively assessed by the following worst case model of the thermal load in the isolating region. Using for example nitrous oxide as refrigerant the temperature in the boiling chamber is determined by the boiling temperature which is close to −90° C. at ambient pressure. Experiments performed by the inventors show that the temperature difference between the boiling chamber and the inner tubing surface can hardly be reduced below 15° C. by improving isolation. Thus, in the worst case model the thermal resistance of the inner surface is described by the smallest expected temperature difference of 15° C. leading to a temperature of −75° C. at the inner surface. As described above a quantitative estimate of the heat transfer property is obtained by $a=\lambda_c/d$. Note that the physical dimension of a is identical to the dimension of the heat transfer coefficient between a solid body and a liquid comparable to water or blood.

Assuming that wall thickness is relatively small compared to the diameter of the tubing an estimate of the heat transfer p (W/m$^2$) across the surface is obtained by $p=\Delta T/(1/a+1/\alpha(T))$.

Here $\alpha(T)$ is the temperature dependent heat transfer coefficient which displays an essentially step like decrease when the surface temperature drops below the freezing temperature of the liquid and $\Delta T$ is the temperature difference between the inner boiling chamber surface and the blood temperature.

FIG. 20 shows the heat transfer computed for polyurethane tubing (0.2 W/mK) of varying wall thickness d assuming a steplike change of the heat transfer coefficient from $\alpha_{min}=2000$ W/m$^2$K to $\alpha_{max}=5000$ W/m$^2$K at a freezing point of −5° C. (data for a physiological saline solution mimicking circulating blood). For a small wall thickness (interval A) the solid body surface temperature is below the freezing point and heat transfer to liquid occurs with $\alpha_{max}$. At the border between intervals A and B the surface temperature reaches the freezing point. In interval B further increasing of wall thickness now reduces the heat flow quickly as the solid body surface temperatures remain constant and the temperature dependent heat transfer coefficient $\alpha(T)$ drops from $\alpha_{max}$ to $\alpha_{min}$. Note that here both a and $\alpha(T)$ decrease as wall thickness increases. At the border between intervals B and C heat transfer coefficient equals $\alpha_{min}$. When wall thickness is further increased (interval C) the heat transfer coefficient remains constant and the reduction of heat transfer is only due to the increase of a as the solid body temperature now increases above the liquid's freezing point. To highlight this observation the derivative of the heat transfer by wall thickness is depicted in FIG. 21. Note that there is a steplike reduction of this derivative when crossing the border from interval B to C. This indicates that any further thickening of the isolation will only result in a modest improvement. Recognizing that space is generally limited in medical applications the interval border to solid body freezing temperatures above the liquid freezing point is a valid indicator for thermal isolation dimensioning. Note that for numbers given above a=1200 W/m$^2$K at the interval border between B and C.

It is believed that the heat transfer coefficient $\alpha_{min}$ depends on local blood flow velocity. Here the investigated value of $\alpha_{min}=2000$ W/m$^2$K is a model for slow blood flow which yields a high value for the heat transfer parameter a at the interval border between B and C. Thus, choosing a ≤1200 W/m$^2$K also for higher blood flow velocities it will be ensured that no ice formation starts at the outer surface as a is sufficiently small compared to $\alpha_{min}$.

In an in-vivo study an elongated transmural lesion of 6 cm length was created with a cryoapplicator of constant wall thickness of 0.11 mm. Here the thermal conductivity of the material was 0.2 W/mK yielding a constant heat transfer parameter of 1820 W/m$^2$K (no distinction between thermally isolating and conducting area). In this experiment the refrigerant flow rate had to be increased by 12% above the maximal tolerable value (increased boiling chamber pressure). Also, this data indicates that choosing a ≤1200 W/m$^2$K in the thermally isolating region will provide sufficient isolation for the creation of elongated lesions at acceptable refrigerant flow rates.

FIG. 22 shows an ablation device 2500 according to an exemplary embodiment of the invention which also includes an ablation applicator 2502. In FIG. 22 it is shown how the ablation device 2500 is inserted into a kidney artery 2510. The ablation applicator 2502 which is configured for cryogenic ablation comprises a tubular body 2504 which defines an inner lumen to which an ablation medium is conductible. The tubular body 2504 may be configured as in any of the embodiments described herein and may or may not have a matrix with particles accommodated therein. The ablation medium may be a cooling agent supplied via a supply element 2506. At an end of the tube 2504 a rounded element 2508 is provided to prevent injury of tissue.

A control mechanism of the ablation applicator 2502 is configured for converting the tubular body 2504 from an elongated operation mode (as one example of a passive operation mode in which no ablation is executed) as shown in FIG. 22 into a spiral operation mode (as one example of an active operation mode in which ablation is or can be executed) shown in FIG. 23.

The control mechanism for performing the conversion between the operation modes of FIG. 22 and FIG. 23 may be an extrinsic mechanism which is provided by a separate member. For instance, a not shown mechanical arrangement may allow performing this conversion. However, alternatively it is also possible that the control mechanism is an intrinsic one. For example, the tubing 2504 may be made of a shape memory material which is configured so that the tube is usually or in a default mode in the elongate state of FIG. 22. However, due to the temperature increase when inserting the tube 2504 into the body may change the configuration so that the configuration is converted from FIG. 22 to FIG. 23.

With the shown embodiment it is possible to ablate tissue of the blood vessel along a helical path of the spirally wound tube 2504 which results in a basically cylindrical ablation area. This is shown in the detailed drawing of FIG. 23. In section 2600 in which the spiral wound tube 2504 is oriented during the ablation procedure, the tissue will be ablated. However, in connected portions 2602, 2604 of the blood vessel 2510 no oblation occurs.

As an alternative to an ablation along a cylindrical ablation area as shown in FIG. 23, it is also possible to ablate tissue simultaneously at different ablation positions being spaced from one another. For example, an ablation applicator may be placed along a defined trajectory into a blood vessel of a kidney so that multiple ablation spots (resulting in punctual lesions) are defined by individual highly thermally conductive surface portions of the ablation applicator. In one subsequent ablation procedure (for instance with one common freeze), all spots may be activated so as to form the multiple ablated tissue portions at the same time.

It should be noted that the term "comprising" does not exclude other elements or steps and the "a" or "an" does not exclude a plurality. Also elements described in association with different embodiments may be combined. It should also be noted that reference signs in the claims shall not be construed as limiting the scope of the claims.

As it has been described above for creating a continuous lesion along the applicator tubing the spacing between the refrigerant exit holes in the refrigerant supply tubing must be sufficiently small. Thus, for creating a lesion of several centimeters of length, a relatively large number of openings must be foreseen. FIGS. 24a to 24c refer to exemplary embodiments for refrigerant distribution for the creation of a continuous elongated lesion.

FIG. 24a shows a schematic arrangement of refrigerant exit holes or openings (also referred to as recesses) 2421, 2422, 2423 and 2424 in a supply tube 2401. The refrigerant is guided along an inner lumen 81. The portion containing the openings for evenly distributing the refrigerant is called distribution structure 2402. The drawing is not to scale. While the diameter of the openings is typically in the order of 10 μm to 100 μm, the distance between the openings is typically in the order of a few to several millimeters. The figure is shown such that the relation of opening diameters is shown qualitatively.

For the embodiment shown in FIG. 24a, nine pairs of radial openings form three groups 2421, 2422 and 2423 of three distinct diameters. Additionally, one single axial distal opening 2424 is formed by a nozzle like structure 2425 on the very distal end of the refrigerant supply line. Each of the three groups contains three pairs of radial openings and for each group the diameter of the openings is essentially kept constant. The most proximal group 2421 has the smallest opening diameter, while the most distal group 2423 has the largest radial opening diameter for compensating the pressure drop along the supply line. The diameter of the single axial distal opening is larger than the diameter of any of the radial openings. Arrows are used for indicating mass flow rate at various locations of the distribution structure. The length of each arrow qualitatively yields an indication of mass flow.

The single most distal opening 2424 is the only "axial" opening meaning that the direction of flow at this opening is essentially in an axial direction of the tubing. All remaining openings 2421 to 2423 are radial openings meaning that the direction of flow is essentially in a radial direction.

FIG. 24b shows the pressure inside the supply tube 2401 and along the long axis of the supply tube 2401. In a distal portion of the tubing three groups 2421, 2422 and 2423 of radial openings and the single axial distal opening 2424 are foreseen. Proximally from the cooled distribution structure 2402 the supply tube 2401 guides the refrigerant flow. Here no exit holes or openings are foreseen and this portion of the tubing is called guiding structure 2403. Without being bound to a specific theory, a pressure curve 2410 for the pressure inside the supply tube is shown for operation at an essentially constant refrigerant flow rate. The abscissa of the plot is a length along the long axis of the tubing. On the ordinate the pressure inside the tubing is shown. In the proximal portion a relatively small pressure drop along the length of the tube is shown. The supplied refrigerant is precooled to a temperature below the ambient (i.e. refrigerant tank temperature). Therefore, at the proximal end of the supply line the refrigerant is in its liquid phase even at a pressure slightly below the tank pressure 2411. As the pressure drops along the line, it will fall below the boiling pressure 2412 in a location 2413. The dimensions of the tubing are designed such that this location 2413 is located at the guiding structure segment of the tubing—i. e. it is located between the most proximal end of the supply tube and the most proximal refrigerant opening.

Below the boiling pressure of the medium the refrigerant will merge in a mixed phase condition of liquid and gaseous refrigerant. Thus, the density of the supplied refrigerant decreases along the line and, therefore, flow velocity increases for maintaining mass continuity along the flow path. This effect increases the pressure drop along the supply line and, thus, further increases the gas content and flow velocity in the very distal portion of the guiding tube 2403. If the supply tube is thermally sufficiently insulated to the ambient the specific enthalpy remains approximately constant along the supply path and gas content can be estimated from pressure using a proper fundamental equation of state for the refrigerant. Accurate fundamental equations of state for a large number of industrial fluids are listed for example in [EW Lemmon & R Span, Journal of Chemical Engineering Data 51: 785-850 (2006)].

For distributing the refrigerant evenly over all refrigerant openings 2421 to 2424, the pressure variation between the openings should not become too large. Furthermore, the pressure at the distal axial opening 2424 of the tubing should remain sufficiently high. FIG. 24c shows a concept for properly influencing pressure in the distal region of the supply tube. The total opening area Ato is the sum of all individual opening areas 2421-2424. Thus, for the embodiment shown in FIGS. 24a to 24c containing 9 opening pairs and one distal axial opening it is the sum of all 19 cross-sectional areas. The supply line cross-section Asc is the area of the cross section of the supply line 2403 or in other word the size of the supply lumen 81.

For ensuring that a sufficiently high pressure is maintained at all refrigerant openings (i.e. also at the most distal one 2424), it is of advantage that the total opening area Ato is smaller than the supply line cross-sectional area Asc. Particularly, in one embodiment Ato may be smaller than 80% of Asc and more particularly Ato may be smaller than 65% of Asc. By this choice the entire opening area of the distribution structure 2402 is smaller than the cross section of the distal portion of the guiding tube 2403. Thus, the distribution structure composes a narrowing in the flow pathway which contributes to maintaining sufficiently high pressure for uniform distribution of cooling power.

For achieving uniform cooling power distribution, the unavoidable pressure drop along the distribution structure 2402 should be kept as small as possible. This is of particular importance as the refrigerant is in a mixed phase condition (i.e. near or in a boiling condition). Thus, any pressure drop along the distribution structure will increase the gas content in the distal portion of the cooling structure (e.g. isenthalpic expansion). As can be seen from FIG. 24a, the cross-sectional area Asc of the supply tubing 2403 is maintained also in the distribution structure 2402. Note that at every opening or pair of openings a portion of the entire refrigerant flow is distributed to the outside. This means that distally from each opening or pair of openings the remaining mass flow rate is smaller compared to a portion proximally from each opening or pair of openings. In FIG. 24a the continuous reduction of mass flow from proximal to distal is indicated by a shortening of arrows inside the distribution structure. The reduction of flow rate contributes to a reduction of flow velocity and, therefore, also to a reduction of pressure drop. This is indicated in FIG. 24b by a flattening of the pressure curve inside the distribution structure 2402. Note that FIG. 2402 shows a schematic picture of the effect as the drawing is not to scale. Typically, the length of the supply line 2401 will be in the order of 50 cm to 200 cm while the length of the distribution structure is in the order of 2 cm to 15 cm. The cross section of the distribution structure is chosen sufficiently large for obtaining sufficient residual pressure at the distal end of the supply tube.

In some embodiments the cross section inside the distribution structure may be larger compared to the cross section of the guiding tube for further reducing the pressure drop within the distribution structure.

If the gas content in the mixed phase refrigerant at the distal end of the guiding portion 2403 is relatively high, the density of the refrigerant is relatively low which will contribute to an undesirably large pressure drop in the distribution portion 2402. This may lead to a significant loss of cooling power in the distal portion of the distribution structure 2402. This distal loss of cooling power may be detected by a thermocouple 2441a or 2441 b located in the distal portion of the distribution structure. For re-establishing a more even distribution of cooling power, the gas content may be reduced by pre-cooling the refrigerant in the cryo-console to lower temperatures. This reduces the gas content at a given pressure. Thus, the pressure drop inside the distribution structure is reduced by more pre-cooling. Generally, the catheter will consume a higher flow rate (and, thus, also more cooling power) when operated at a constant supply pressure with more pre-cooling. If an increased flow rate is not intended (for example for when operating the catheter at a desired specified cooling power), the supply pressure delivered by the console may be reduced.

Using for example nitrous oxide as the refrigerant, the supply pressures will typically be in the range of 35 bars to 55 bars absolute. Precooling of the medium to approximately 0° C. relates to a boiling pressure 2412 of approximately 30 bars. The pressure in the boiling chamber of the catheter (lumen 80 in FIGS. 1 and 14) is typically in the range of 0.88 bars to 2 bars. Therefore, a pressure of a few tens of bars or a few bars may be sufficient for driving the refrigerant flow across each opening. Thus, inside each opening the pressure is significantly smaller than the boiling pressure of the refrigerant. In consequence, the density of the refrigerant inside the distribution structure and inside each opening is small and flow velocity is high. In particular inside the openings, the flow velocity of the mixed phase refrigerant may be close to the sonic speed of the mixed phase refrigerant. Generally the sonic speed in a mixed phase medium is larger compared to the pure gas phase. Therefore, the size of the openings may be designed such that flow velocity in all openings or in a majority of openings is above the sonic speed of the gaseous phase. Using nitrous oxide as the refrigerant, the sonic speed of the gaseous medium at −85° C. (boiling point near atmospheric pressure) is approximately 215 m/s. The openings may be designed so narrow that the mixed-phase refrigerant inside the openings exceeds the sonic speed of the gas phase.

Summarizing, for creating a continuous elongated lesion the spacing of the refrigerant openings in the distribution structure of the supply tube must be sufficiently small. While a small spacing increases the number of openings, care has to be taken that the total opening area Ato remains sufficiently small such that the sum of all openings still forms a narrowing in the flow pathway. For evenly distributing a refrigerant in a mixed liquid-gas condition, the opening may be designed narrow enough that flow velocity inside the openings exceeds the sonic speed of the gaseous refrigerant.

In FIG. 24a one single axial opening 2424 at the very distal end of the distribution structure 2402 of the supply line is foreseen. A nozzle like component 2425 is used for adjusting the area of this single most distal opening. As shown in FIG. 24c, the distal axial opening 2424 is chosen to be largest of all openings. When using pairs of openings along the distribution structure 2402, the area of the most distal opening 2424 may be at least the sum of both areas of the most distal opening pair 2423. This ensures that a sufficient refrigerant flow is maintained at the most distal opening. However, the most distal opening may not be larger than 100 μm and the total cross sectional area Atc still needs to be smaller than the cross-sectional area Asc of the guiding tube 2403.

A single distal axial opening 2424 may offer another advantage of practical value. The refrigerant openings are typically very small structures with sizes down to 10 μm. Thus, there is a potential danger that tiny pollutions, in particular dust particles or other particular matter (i.e. particle shaped matter, not to be confused with the "particles" accommodated in a matrix of a tubular body as described at other instances herein) included in the refrigerant may block or jam the openings. This may alter refrigerant distribution along the target area in an undesired fashion and hamper the correct creation of a continuous elongate lesion. Therefore, particle filters are built in inside the cryo-ablation console and catheter devices are built in a clean room environment. However, occurrence of tiny pollutions cannot be fully excluded. Filters eliminate particular matter only above a given size. Clean room production minimizes the number of particles below a certain value but does not exclude every single particle. Furthermore, even in a sterile hospital environment a tiny particle may enter the supply line when attaching the cryo-catheter to the cryo-console (for connecting the catheter to the console protection covers need to be removed).

For the shown embodiment structure 2425 is shaped such that at its proximal end a nozzle is shaped such that the diameter decreases in a conic portion continuously to the final opening parameter. In other embodiments, also at the distal end a conic structure may be foreseen such that structure 2425 may appear symmetric in the axial direction. That may be of advantage for production of the device. Note that it is difficult to insert such a tiny nozzle in the build process with proper orientation. A symmetric structure overcomes this problem. In certain embodiments, however, a cone portion may be omitted and the nozzle structure may be essentially a hollow cylinder with a given inner diameter.

When performing a freeze, the refrigerant flow may transport such a tiny particle along the guiding tube 2403 to the distribution structure. Due to the individual sizes of the openings and the refrigerant flow pattern inside the tube, such a particle may be flushed towards the very distal end of the distribution structure 2402. By designing this opening such that it is also the opening with the largest cross section sufficiently small particles (e.g. particles smaller than 100 µm) can be washed out from the distribution structure without blocking any of the openings. As can be seen from FIG. 1 outside the supply tubing the applicator tubing 10 seals the refrigerant pathway from the environment and, thus, also from the body of a patient. As lumens in the low pressure lumen 80 are significantly larger compared to the supply lumen 81 of a catheter, flushing a small particle (e.g. smaller than 100 µm) to the low pressure draining does not impose any problem for the function and the safety of the device.

A slightly larger particle (e.g. slightly above 100 µm) may be small enough that it can be transported along the guiding line 2401 and the distribution structure 2404 but it may be too large for passing the single distal axial opening 2424. Such a particle may get stuck in the single distal axial opening, partially blocking the cross-section and reducing the flow to the very distal end of the elongated lesion. However, there are situations were such a partial failure condition is still acceptable. Such a partial blocking of the distal refrigerant flow results in a reduced cooling power at the very distal end. Particularly, in an application where many openings are used for creating an elongated lesion a reduction of cooling power restricted to a small area at the very distal end may be tolerable. The catheter as a therapeutic device may be designed such that lesions are somewhat longer than needed for therapeutic efficiency for ensuring a positive outcome. Furthermore, diagnostic techniques, such as catheter mapping of electric intra-cardiac signals, may be used for controlling efficiency of cryo-ablation. In such a situation, a potentially incomplete lesion may be closed by repeating freezing after repositioning the catheter.

However, even if a partially blocking of the most distal axial opening may be tolerable, it is desirable to control refrigerant flow to the most distal end of the supply structure. Therefore, a thermocouple 2441*a* or 2441 *b* may be foreseen in the distal portion of the distribution structure. In one embodiment, a thermocouple 2441*a* may be located a few millimeters (e.g. 1 to 5 mm) distally from the single distal axial opening 2424. In such a situation it may essentially record the effect of the flow at the axial opening 2424. Warmer temperatures at this distal thermocouple may indicate partial or even complete blocking of the axial opening 2424. As described above, when using nitrous oxide as a refrigerant, the boiling pressure may be close to −85° C. Therefore, relatively cold temperatures are expected when boiling a mixed-phase refrigerant at the distal end of the applicator. Partial blocking of the distal openings (for example due to a particle or due to insufficient pressure in the distal distribution structure) will lead to a reduction of local cooling power. As a consequence, the refrigerant may boil out completely in the surrounding of the distal thermocouple. Therefore, the recorded temperatures will be above the boiling point. Proper thresholds may be used for defining an accepted degree of partial blocking. When using nitrous oxide as a refrigerant, values in the interval of −70° C. to −40° C. may define a proper threshold.

In one embodiment, a pollution filter may be foreseen in the connector of the catheter adapted for connection to the cryo-console. Such a pollution filter may be adapted such that the pieces which can pass the filter are smaller than the diameter of the distal axial opening.

The position of a distal thermocouple, however, may not be restricted to a location near the most proximal opening. In certain embodiments, a thermocouple 2441*b* may be placed anywhere in the most distal half of the refrigerant distribution structure or more specifically anywhere in the most distal quarter of the refrigerant distribution structure. Such a choice of locating the sensor 2441*b* in a distal segment but not at the very distal end may be of advantage when it should be less affected by a partial blocking of the most distal axial refrigerant opening. In such a situation, the distal thermocouple sensor is mainly used for monitoring if there is sufficient pressure in the distal refrigerant distribution structure for evenly distributing refrigerant at all radial openings or openings.

In some embodiments, a distal axial opening 2424 may not be used. It may be of advantage to completely block the distal end by a simple manufacturing process such as gluing. In such an embodiment containing only radial refrigerant openings 2421 to 2423, a thermocouple 2441*a* at the very distal end of the line may not be properly cooled by the refrigerant. Therefore, a distal thermocouple 2441*b* may be located in another location in the distal portion.

In the proximal portion of the refrigerant distribution structure the pressure inside the supply tube is slightly higher and the probability of closing openings by particles is lower. However, it is of advantage to use also a sensor 2442 in this segment. In the proximal portion of the refrigerant distribution structure the pressure difference between the lumen 81 inside and the lumen 80 outside of the supply tube is relatively high and therefore, when properly designing the dimensions of all openings refrigerant flow in the proximal segments is stable. With other words in the proximal segment varying operation parameters, such as supply pressure of the console, precool temperature of the refrigerant or local blocking of opening by an unavoidable particle do have less influence compared to the distal portion. Therefore, the temperatures recorded by a proximal thermocouple are highly reproducible. With proper dimensioning of the holes it can be ensured that over a wide range of operation parameters the proximal thermocouple is surrounded by mixed phase boiling refrigerant. For a mixed phase refrigerant the recorded temperature is close to the pressure dependent boiling point of the refrigerant.

Therefore, the temperature recorded at the proximal thermocouple allows for a relatively stable monitoring of the pressure in the proximal return pathway of the cryo-applicator. For ensuring the functional safety of the ablation catheter it may be of advantage to monitor the proximal temperature with lower limits compared to the distal temperature. When using for example nitrous oxide as refrigerant temperature, values in the interval of −85° C. to −70° C. may define a proper threshold.

In certain embodiments, a third thermocouple 2443 may be used which is located in the back stream of the refrigerant flow i.e. proximally from sensor 2442 and outside of the guiding tube 2403. More specifically, the sensor 2443 may be located more than 1 cm proximally from the most proximal refrigerant opening and even more specifically it may be located more than 2 cm from the most proximal refrigerant opening. Thus, the backstream thermocouple 2443 is located in a location distant from the distribution structure. During normal operation the refrigerant may be boiled out completely near sensor 2443 and rewarmed significantly above the boiling point of the refrigerant. Therefore, the measurement at sensor 2443 may be used for controlling refrigerant supply such that all refrigerant in the back stream is boiled out completely. Using nitrous oxide as the refrigerant, temperatures above −60° C., and more particularly −40° C., may define a proper threshold.

FIGS. 25a to 25e show another embodiment of a supply tube 2501 with a distribution structure 2502. The distribution structure 2502 contains two groups of radial openings 2521 and 2522 and one distal axial opening 2523. FIG. 25a shows the entire supply tube 2501 to scale and therefore, the openings in the distal portion are not visible. A hatched arrow marks the location of the most proximal radial opening. The distribution structure 2502 is essentially the portion from the distal axial opening to the most proximal radial opening. The entire length of the tube 2501 is 1500 mm. The outer diameter of tubing 2501 is 0.35 mm. Therefore, it appears as a narrow line in the drawing. The length of the distribution structure 2502 is approximately 65 mm.

FIG. 25b shows the distribution structure 2502 at a scale which is increased by more than a factor of 20 compared to FIG. 25a. There are in total twelve pairs of radial openings. The proximal radial group 2521 contains seven pairs of openings and the distal radial group 2522 contains five pairs of openings. At this scale the openings appear as tiny dots. Again the most proximal radial opening pair is marked by a hatched arrow. At the distal end an axial opening 2523 is foreseen. This axial opening is formed by an approximately 2 mm long structure 2524 (shown only in FIG. 25e). The opening inside this structure is indicated by a hatched line.

FIG. 25c shows a cross section of a proximal pair of openings from the group 2521. Scale is increased by more than a factor of 30 compared to FIG. 25b. One opening is labeled 2521a while the opposite opening is labeled 2521b. As openings may be produced by laser cutting or laser drilling the diameter of opening 2521a may be chosen slightly larger than the diameter of opening 2521b. That offers the advantage that first opening 2521a is made at a slightly larger diameter. After that a slightly thinner laser beam is directed across opening 2521a for producing opening 2521b which a slightly smaller diameter.

Similarly, FIG. 25d shows a cross section of a distal pair of openings from the group 2522. Again on one side of the tubing a diameter 2522a is chosen slightly larger compared to the diameter 2522b due to production techniques. For distributing the refrigerant equally over the entire length of the distribution structure 2502, distal openings 2522 should be made larger compared to proximal openings 2521. This means with respect to the slightly different diameters chosen on both sides of the supply tube 2501 that the sum of areas of a pair 2522a and 2522b is larger than the sum of areas of a pair 2521a and 2521b. The inner diameter of the supply tube 2501 is 0.25 mm.

When using openings with an essentially circular cross-section, the area is proportional to the square of the diameter. However, considering also the flow velocity profile across such a cross-section, the influence of the diameter on the mass flow becomes even stronger. For example for a laminar flow profile the entire flow at an opening is theoretically proportional to the fourth power of the diameter. Therefore, the flow across a circular opening for a given diameter will strongly depend on the diameter (dependency of second to fourth power). This means with other words that at a given pressure, an increase of the diameter by 10% increases the mass flow across an opening by approximately 20% to 40%. Therefore, when designing radial openings, the diameter should not be increased in too large steps from proximal to distal. On the other hand, openings can be manufactured only with a certain tolerance which may be in the order of a few microns. Therefore, they cannot be increased in very tiny steps.

For the embodiment shown in FIGS. 25a to 25e, the nominal diameters of the proximal opening group 2521 may be 42 μm for opening 2521a and 37 μm for opening 2521b. For the distal opening group 2522, the nominal diameters may be 50 μm for opening 2522a and 45 μm for opening 2522b. It should be stressed that in this context there are small unavoidable variations when comparing mass flow at individual openings. For each group 2521 and 2522, the flow at an individual opening pair may be slightly larger for proximal opening pairs of a group compared to more distal opening pairs of the same group. However, such small variations can be accepted when the variations are small enough for allowing the creation of a continuous lesion. From a practical point of view it may be of advantage to use only a few (two or three) groups of radial openings with essentially constant size in each group. It may simplify the production of the device.

It may be of advantage to use pairs of radial openings for distributing the refrigerant approximately equally around a supply tube. That may be of benefit for assembly of the catheter. The supply tube may be inserted into the applicator tube without any need for controlling the orientation of the tiny openings relative to an azimuthal angle of the outer applicator tube (for example applicator tube 10 in FIG. 14). However, in other embodiments, instead of pairs of radial openings, multiple single radial openings may be distributed along the distribution structure. In yet another embodiment, instead of pairs, triples of openings (or subgroups of even more than three) may be used along the distribution structure.

When using an axial opening on the sole distal end of the distribution structure, it is advantageous to incorporate it by one single distal opening. A nozzle structure 2524 may be used for creating an opening of defined diameter. A sealing 2525 may be used for closing the space between the nozzle 2524 and the supply tube 2501. In certain embodiments, for example glue may be used for creating the seal. In other embodiments, the outer surface of the nozzle structure may contain ridges or lamellas for creating a seal.

Referring again to FIGS. 25a to 25e the radial openings are arranged in pairs. Thus, it is reasonable to choose the area of the distal axial opening 2523 such that it is at least the sum of the areas of the areas of a distal opening pair 2522a and 2522b. As the pressure is smallest at the very distal end of the distribution structure, its area may also be slightly larger than the sum of opening areas 2522a and 2522b. Thus, the distal axial opening has the largest diameter which is of advantage for flushing tiny particles across this distal opening. For the embodiment shown in FIG. 25e, the nominal diameter of the distal opening may be 72 μm.

From the dimensions listed above, the cross-sectional area Asc of the supply tube 2501 is estimated to be 0.049 mm$^2$. The total opening area Ato is estimated to be 0.039 mm$^2$ and, thus, smaller than the cross-sectional area. Using nitrous oxide as the refrigerant, the boiling chamber pressure may be selected to be near 1 bar. From the adiabatic coefficient of nitrous oxide, one may estimate that the pressure inside the boiling chamber may be near 2 bars. For creating a continuous lesion, a cooling power of approximately 60 Watts may be distributed along the distribution structure 2502. The fundamental equations of state as described for example in [EW Lemmon & R Span, Journal of Chemical Engineering Data 51: 785-850 (2006)] may be used for estimating thermodynamic properties of nitrous oxide. When precooling the refrigerant to 0° C. at 50 bars, a flow rate of 0.3 g/s is needed for achieving 60 Watts assuming isenthalpic expansion along the supply tube 2501. From the fundamental equation of state, a density of 14 kg/m³ is obtained at 2 bars. From this data a mean velocity of approximately 550 m/s is computed across Ato. Note that this velocity is in-between the sonic speed of the gas-phase (215 m/s) and the liquid phase (1060 m/s). Therefore, the mixed phase velocity can exceed the sonic speed of the gas phase.

In FIG. 25b, the spacing between radial openings is 5 mm and kept constant but the area of the openings is increased from proximal to distal. However, in another embodiment, the area may be kept constant and spacing may be decreased from proximal to distal. In yet another embodiment, a combination of varying opening size and spacing may be used. In certain embodiments, the shape of the openings may not be circular. Openings of quadratic, rectangular, oval or slit like shape may be used. Regardless of the shape of the openings, the total opening area Ato is kept smaller than a cross-section of the supply tubing.

FIG. 26 shows a cross section of a distribution structure 2602 inside the cryo-applicator 10. While FIGS. 1 and 14 show a cross section of the short axis of the embodiment FIG. 26 shows a cross section of the long axis. The distal and proximal portion of the distribution structure 2602 is shown inside an applicator tube 10 supported by a helical coil 30. A nitinol wire 50 is guided inside the applicator tube 10. While in the schematic FIG. the cryo-applicator appears straight it may be bend by the nitinol structure to a curved shape as can be seen from FIGS. 2A and 3. A most proximal radial opening 2621 is shown. A thermocouple 2642 is used for measuring the temperature near the proximal opening 2621. A fixation 2652 such as a gluing spot or a shrink tubing is used for holding the thermocouple in position. The fixation 2652 is located a few millimeters proximally from the opening 2621 for ensuring, that the opening is not unintendedly closed by the fixation 2652.

Furthermore, a most distal radial opening 2622 and the distal axial opening 2623 are shown. The distal axial opening 2623 is formed by a narrow tube like structure fixed inside the distal end of the supply tube 2601. A thermocouple 2641 is used for measuring the temperature in the distal distribution structure. A fixation 2651 is used for holding the thermocouple in position relative to the openings. Note that for the shown embodiment, the location of thermocouple 2641 may also define the minimal distance of the distal axial opening from the stopper. This may be of advantage for ensuring correct positioning of the distribution structure relative to the stopper during production.

For controlling the distribution of cooling power in the distal portion of the applicator tubing, a stopper structure 2650 is foreseen. This stopper structure prevents that a refrigerant flow from a distal opening unwantedly may be distributed in a very distal portion of the tube which is not intended for therapeutic use. Note that such a stopper structure is not only of advantage in combination with an axial distal opening. Generally, it is of advantage to block any refrigerant flow to a therapeutically non-active segment for safety reasons. Using a stopper structure 2650, a leakage in a distal, therapeutically non-active tube may not allow for an undesired escape of refrigerant. Therefore, in addition to the stopper structure 2650, also additional sealing structures such as glued connections may be used (not shown in the image). The stopper structure as shown in FIG. 26 fulfills a double function. It defines the distal end of the chilled segment and therefore the distal end of the therapeutically active segment of the tubing. Furthermore, it limits refrigerant flow to a more distal therapeutically passive portion. For ensuring a complete sealing additional blocking or stopping structures may be used.

In the return path between the supply tube and the outer applicator tube the refrigerant streams in an essentially axial direction from distal towards proximal. Therefore, also outside the supply tube a difference in pressure may be observed. Generally, the return pressure may be higher in a distal portion 80a of the applicator tube while it will be lower in the proximal portion 80b. However, for evenly distributing refrigerant along the distribution structure, also this pressure difference should be kept low. Therefore, the cross-section of the return or draining lumen 80a and 80b is significantly larger compared to the cross section of the supply lumen. Here, draining refers to an active low pressure evacuation as described above.

Referring now to FIGS. 27a to 27c, cryo-applicator embodiments for creating elongated lesions are shown. These embodiments may be of advantage when instead of a boiling medium a high heat capacity cooling medium is used. For example essentially any medium in a thermodynamic condition near its critical point has a relatively high heat capacity. If the critical point temperature of a medium is low enough for cryo-ablation (i.e. significantly colder than a freezing point of tissue), it can be precooled outside the body and supplied to the cryo-applicator using a thermally isolating structure. Methods for providing such near critical point refrigerant are described e.g. in U.S. Pat. No. 8,387,402 B2. Cryo-ablation catheters using a high heat capacity refrigerant are described e.g. in WO 2016/196066 A2 and US 2017/0151008 A1. However, it may be of advantage to provide methods which allow distributing the cooling power of a high heat capacity refrigerant evenly along an elongated cryo-ablation applicator.

Such a high heat capacity refrigerant can be guided across a cryo-applicator and it rewarms due to the heat exchange with the ambience. However, due to the high heat capacity the unavoidable increase of temperature is small enough for keeping its temperature well below a freezing point of tissue. Furthermore, different from the embodiments described above, the density and pressure of a high heat capacity refrigerant does not significantly change during rewarming due to cryoablation. Therefore, the cross-sections of the supply and return path may be chosen with a similar dimension.

FIG. 27a shows an exemplary embodiment for a cryo applicator 2710 using a high heat capacity refrigerant. An inner lumen 2701 is used as a supply line. An outer lumen 80 may define the return pathway. Here supply and return are arranged in a coaxial fashion. The supply line 2701 may be made from a plastic which is thermally isolating. Therefore, it limits the heat flow from the return lumen 80 to the supply lumen 81. As pressures in both lumens 80 and 81 are similar, a wide range of plastics including polyamide, polyurethane or the like may withstand the relatively low mechanical stress. However, in certain embodiments, mechanically more robust plastics such as polyimide or PEEK may be of advantage. In one embodiment, the supply line 2701 may contain only one distal axial opening and the opening diameter may be identical to the supply line diameter. A stopper structure similar as described in FIG. 26 may define a distal end of the therapeutically active segment of the applicator tubing. The outer return lumen is defined by a support structure or support tubing 30. Similar as in FIG. 14, this structure 30 supports the applicator tubing 10. However, when using a high heat capacity refrigerant, the pressure in the return lumen 80 may be relatively high and additional safety measures are needed for preventing the escape of refrigerant into the body or the ambience.

Therefore, support structure 30 is a tube and may be made from a metallic material and may be designed for withstanding a high burst pressure. In some embodiments, this burst pressure may be at least twice normal operation pressure of the return lumen. When using a shape-memory material such as for example nitinol, tubing 30 may take a double function. It withstands the relatively high refrigerant pressure and it may define a predefined curved shape of the applicator tubing, such as shown in FIGS. 2A, 2B and 3.

Using for example near critical nitrogen as a refrigerant, the critical point temperature is approximately −147° C. This yields a temperature difference or gradient of approximately 184° C. relative to a tissue of a human or an animal. The refrigerant may be supplied to the applicator with a temperature approximately 30° C. colder than the critical point temperature and it may be removed from the applicator at a temperature approximately 30° C. warmer than the critical point temperature. Thus, the temperature gradient of the high heat capacity refrigerant relative to the body may vary by approximately ±16%. This variation may be small enough for creating a continuous elongated region. In certain embodiments the supply tube 2701 may also contain a plurality of radial openings for creating a more uniform temperature distribution along the applicator.

At such a high temperature gradient from refrigerant to tissue of more than 100° C., proper measures may be of advantage to distribute heat flow evenly along the target region of the applicator. Otherwise, a high cooling power may be achieved at the very distal end of the cryo-applicator 2710 while, due to rewarming, less cooling power is obtained at the proximal region of the cryo-applicator 2710. Furthermore, at such a large temperature gradient, lesions of a maybe undesired large thickness may potentially damage tissue adjacent to the target tissue. For example, when treating atrial fibrillation by ablation, care has to be taken, that anatomical structures adjacent to the left atrium, such as the phrenic nerve or the esophagus, are not damaged.

Therefore, an outer applicator tubing 10 may be foreseen for reducing heat flow to a desired value. Similar as described in FIG. 14, thermally conducting particles may be added to a portion which is preferably in contact with the tissue 92. However, in certain embodiment a uniform thermal conduction may be chosen along the circumference as sufficient cooling power may be supplied by the high heat capacity refrigerant. For further increasing the safety of the device, a vacuum lumen 2727 may be included between the tubing structure 30 and the outer applicator tubing 10. This lumen has a narrow cross-section but extends along the entire therapeutically active applicator. This lumen may be kept at a low pressure which is monitored by the cryo-console or another external device. In the case of a leak in the tubing 30, a pressure increase can be detected. Thus, refrigerant supply can be terminated immediately and immediate active draining by a vacuum source may be activated. Here draining may involve all lumens filled by the refrigerant in a leak condition: the supply lumen 81, the return lumen 80 and the vacuum lumen 2727. Additionally, the use of the applicator tubing 10 may be of advantage for meeting requirements for ensuring the biocompatibility of the cryo-applicator tubing in contact of the endothelium.

In FIG. 27b, an alternative embodiment for a cryo-applicator 2711 using a high heat capacity refrigerant is shown. Here, instead of a coaxial arrangement, refrigerant supply and return are arranged in a parallel fashion. Two tubes 2701 (supply) and 2730 (return) are used. At the distal end, a connection structure (indicated by a hashed arrow) is used for guiding the refrigerant from the supply to the return pathway. Note that in this example both tubes are built with identical cross sections as the density and the pressure are comparable in both tubes when using a high heat capacity refrigerant. Again, metallic materials may be used and shape memory alloys may define a preselected shape of the applicator tubing. The two tubes may be mechanically connected to each other by a fixation 2750. This fixation may be established by soldering, welding, gluing or the like. The connection may be continuous junction along the length of the tubes or it may be created by distinct spots. Both tubes 2701 and 2730 are covered by an applicator tubing 10 for controlling heat flow from the refrigerant to the ambience. For the shown embodiment, the outer applicator jacket is created such that a space 2728 is filled with a plastic material on a side with is in contact with the target tissue for enhancing heat transfer. On the opposite side, a vacuum lumen 2727 is created. This vacuum lumen 2727 has a double function. It limits heat flow to the blood and allows for leak detection by pressure control. A temperature sensor 2740 may be foreseen inside the vacuum lumen for monitoring temperature during ablation. In certain embodiments, similar as described above, one sensor may be used for measuring a temperature in a distal portion of the applicator tubing 2711 while a second sensor may be used for measuring temperature in a proximal portion.

In FIG. 27c yet an alternative embodiment for a cryo-applicator 2730 using a high heat capacity refrigerant is shown. Here, three tubes 2701a to 2701c provide the refrigerant supply lumen 81 and four tubes 2730a to 2730d provide the return lumen 80. Similar as for the embodiment shown in FIG. 27b, supply and return are connected at the distal end by a connection structure. A single hatched arrow is used for indicating that all tubes 2701a to c and 2730 a to d are in fluid communication at the very distal end by one common connection structure. All supply and return tubes have identical dimensions and they are designed to withstand the same relatively high pressure level. They may be manufactured from a shape memory alloy for defining a preselected shape of the applicator tubing. Fixations 2750 as described in FIG. 27b may be used for connecting the tubes relative to each other.

As the refrigerant rewarms along the flow pathway, its density decreases to some extent and it may be of advantage to use one tube more for the return pathway than for the supply. Note that the total return cross-section is then somewhat larger than the total supply cross-section. As the refrigerant inside the supply tubes is somewhat colder than in the return tubes, they may be arranged in the portion of the applicator tubing which is in contact with the tissue. The return tubes may be arranged in a portion of the tubing which is preferably in contact with the blood flow. This contributes to reducing the heat flow to the blood stream. Note that the fixations 2750 of the tubes relative to each other is made in such a fashion that the lumen 2727 between the tubes is not sealed. The vacuum lumen 2727 may still be used for monitoring and controlling the pressure inside the applicator tube 10. In FIG. 27c, this is indicated by leaving one pair of tubes unconnected in the upper portion of the figure. Alternatively, the connections may not be continuous along the length but the may be interrupted. The tubes may be surrounded by an applicator tubing 10 for adjusting the heat transfer from the refrigerant to the ambience and for providing a mechanical seal around the supply and return tubes 2701 a to c and 2730 a to d. Therefore, a vacuum can be applied to inside the lumen 2727 between the tubes and the pressure can be monitored for detecting a leak in the refrigerant pathway.

Note that therapeutic efficiency and functional safety may impose a certain trade-off. For a high pressure resistance, a large wall thickness is of advantage. In contrast, for adjusting heat transfer to a sufficiently high value, a thinner wall may be of advantage. In one embodiment, particles such as beads, may be added to the polymetric matrix of the applicator tubing for increasing heat transfer while allowing the design of a sufficiently thick wall for meeting safety requirements. In yet another embodiment, particles, such as fibers, may be used for increasing the tensile strength (and, thus, pressure resistance) while keeping the wall of the tubing sufficiently thin. Note that the thickness of the applicator tubing 10 varies for the embodiment depicted in FIG. 27c due to the use of seven tubes. A mean thickness may be used for computing a heat transfer parameter of such a configuration.

For measuring the temperature along the applicator tubing, one or more sensors, such as thermocouples indicated in FIG. 27b, may be used inside the vacuum lumen 2727.

The invention claimed is:

1. An ablation applicator for an ablation device for ablating tissue of a blood vessel, the ablation applicator comprising:
   a tubular body defining an inner lumen to which an ablation medium is conductible, the tubular body comprising a polymeric tubing;
   a control mechanism configured for converting the tubular body between a passive operation mode for inserting the ablation applicator into the blood vessel and an active operation mode for ablating tissue; and
   a plurality of ablation medium supply lines for supplying the ablation medium to the inner lumen, the plurality of ablation medium supply lines being arranged within the inner lumen and having a number of openings for passing the ablation medium from the plurality of ablation medium supply lines to the inner lumen for thermally contacting the ablation medium with the tubular body,
   wherein a circumference of the tubular body comprises a first portion and a second portion, the first portion being configured to contact the tissue and the second portion being configured to be in contact with a blood flow,
   wherein the ablation medium is a mixed phase refrigerant comprising a gas phase and a liquid phase, and wherein an opening area of each of the openings distributed along the plurality of ablation medium supply lines is so small that a flow velocity inside each opening is higher than a sonic speed of the gas phase.

2. The ablation applicator according to claim 1, wherein said plurality of ablation medium supply lines are arranged proximate to the first portion of the circumference of said tubular body.

3. The ablation applicator according to claim 1, further comprising a plurality of ablation medium return lines for discharging the ablation medium from the inner lumen, wherein said plurality of ablation medium return lines are arranged proximate to the second portion of the circumference of said tubular body.

4. The ablation applicator according to claim 1, wherein at least a part of the openings is distributed along the plurality of ablation medium supply lines with a predetermined spacing between neighbouring openings.

5. The ablation applicator according to claim 4, wherein said openings distributed along the plurality of ablation medium supply lines are arranged proximate to the first portion of the circumference of said tubular body.

6. The ablation applicator according to claim 1, further comprising a temperature sensor arranged within the inner lumen and positioned at one of the openings at a proximate end of the inner lumen, and wherein a total opening area of all the openings is less than a cross-sectional area of the plurality of ablation medium supply lines.

7. The ablation applicator according to claim 1, wherein the ablation medium is a high heat capacity cooling medium.

8. The ablation applicator according to claim 3, wherein the number of ablation medium supply lines is equal to or less than the number of ablation medium return lines.

9. The ablation application according to claim 3, further comprising a common connection structure configured to provide fluid communication between distal ends of all ablation medium supply lines and distal ends of all ablation medium return lines.

10. An ablation device for ablating tissue of a blood vessel, the ablation device having an ablation applicator comprising:
    a tubular body encircling a plurality of inner lumens to which an ablation medium is conductible, the tubular body comprising a polymeric tubing;
    a control mechanism configured for converting the tubular body between a passive operation mode for inserting the ablation applicator into the blood vessel and an active operation mode for ablating tissue;
    a plurality of ablation medium supply lines for supplying the ablation medium to one or more lumens of said plurality of inner lumens, wherein said plurality of ablation medium supply lines are arranged inside the polymeric tubing; and
    an ablation medium return line, wherein said return line is arranged inside the polymeric tubing and made from a material that defines the active shape of the applicator,
    wherein a circumference of the tubular body comprises a first portion and a second portion, the first portion being configured to contact the tissue and the second portion being configured to be in contact with a blood flow,
    wherein the ablation medium is a mixed phase refrigerant comprising a gas phase and a liquid phase, and wherein an opening area of openings distributed along the plurality of ablation medium supply lines is so small that a flow velocity inside each opening is higher than a sonic speed of the gas phase.

11. The ablation applicator according to claim 10, wherein said plurality of ablation medium supply lines are arranged proximate to the first portion of the circumference of said tubular body.

12. The ablation applicator according to claim 10, further comprising a plurality of ablation medium return lines for discharging the ablation medium from the inner lumen, wherein said plurality of ablation medium return lines are arranged proximate to the second portion of the circumference of said tubular body.

13. The ablation applicator according to claim 10, wherein at least a part of the openings is distributed along the plurality of ablation medium supply lines with a predetermined spacing between neighbouring openings, and wherein said openings distributed along the plurality of ablation medium supply lines are arranged proximate to the first portion of the circumference of said tubular body.

14. An ablation applicator for an ablation device for ablating tissue, the ablation applicator comprising:

a tubular body defining an inner lumen to which an ablation medium is conductible, the tubular body comprising a polymeric tubing;

a control mechanism configured for converting the tubular body between a passive operation mode for inserting the ablation applicator into the blood vessel and an active operation mode for ablating tissue;

an ablation medium supply line for supplying the ablation medium to the inner lumen, the ablation medium supply line being arranged within the inner lumen and having a number of openings for passing the ablation medium from the ablation medium supply line to the inner lumen for thermally contacting the ablation medium with the tubular body; and an ablation medium return line for discharging the ablation medium from the inner lumen, the ablation medium return line being arranged in parallel with the ablation medium supply line within the inner lumen, wherein the tubular member comprises a heat transfer enhancing member protruding from a part of the tubular member proximate to the tissue and into a space between the ablation medium supply line and the ablation medium return line, wherein the ablation medium is a mixed phase refrigerant comprising a gas phase and a liquid phase, and wherein an opening area of openings distributed along the ablation medium supply line is so small that a flow velocity inside each opening is higher than a sonic speed of the gas phase.

15. The ablation applicator according to claim 14, wherein the heat transfer enhancing member comprises a plastic material.

16. The ablation applicator according to claim 14, wherein the ablation medium is a high heat capacity cooling medium.

17. The ablation applicator according to claim 14, further comprising a connection structure configured to provide fluid communication between a distal end of the ablation medium supply line and a distal end of the ablation medium return line.

18. The ablation applicator according to claim 14, further comprising
a first temperature sensor configured to measure a temperature in a distal portion of the inner lumen; and
a second temperature sensor configured to measure a temperature in a proximate portion of the inner lumen.

* * * * *